United States Patent
Keyser et al.

(10) Patent No.: US 9,707,255 B2
(45) Date of Patent: *Jul. 18, 2017

(54) MICROPOROUS ZIRCONIUM SILICATE FOR THE TREATMENT OF HYPERKALEMIA IN HYPERCALCEMIC PATIENTS AND IMPROVED CALCIUM-CONTAINING COMPOSITIONS FOR THE TREATMENT OF HYPERKALEMIA

(71) Applicant: ZS Pharma, Inc., Fort Worth, TX (US)

(72) Inventors: Donald Jeffrey Keyser, Southlake, TX (US); Alvaro F. Guillem, Lantana, TX (US)

(73) Assignee: ZS PHARMA, INC., Coppell, TX (US)

( * ) Notice: Subject to any disclaimer, the term of this patent is extended or adjusted under 35 U.S.C. 154(b) by 497 days.

This patent is subject to a terminal disclaimer.

(21) Appl. No.: 13/939,656

(22) Filed: Jul. 11, 2013

(65) Prior Publication Data

US 2014/0105971 A1  Apr. 17, 2014

Related U.S. Application Data

(60) Provisional application No. 61/670,415, filed on Jul. 11, 2012, provisional application No. 61/800,291, filed on Mar. 15, 2013.

(51) Int. Cl.
*A61K 33/24* (2006.01)
*A61K 45/06* (2006.01)
(Continued)

(52) U.S. Cl.
CPC .............. *A61K 33/24* (2013.01); *A61K 9/143* (2013.01); *A61K 45/06* (2013.01); *B01J 19/006* (2013.01);
(Continued)

(58) Field of Classification Search
CPC ........ A61K 33/00; A61K 33/24; A61K 45/06; A61K 9/14; A61K 9/143; C01P 2002/72;
(Continued)

(56) References Cited

U.S. PATENT DOCUMENTS 3,329,480 A   7/1967 Young
3,947,279 A   3/1976 Hudecek
(Continued)

FOREIGN PATENT DOCUMENTS

CN   101426477   2/2007
EP   0384728   8/1990
(Continued)

OTHER PUBLICATIONS

International Preliminary Report on Patentability and Written Opinion of PCT/US2013/050071 mailed Dec. 9, 2013.
(Continued)

*Primary Examiner* — Kortney L Klinkel
(74) *Attorney, Agent, or Firm* — Arent Fox LLP

(57) ABSTRACT

The present invention relates to novel calcium-containing microporous zirconium silicate compositions that are formulated to remove toxins, e.g. potassium ions, from the gastrointestinal tract at an elevated rate without removing calcium from the patient's body. Also disclosed are methods of using calcium-free or low calcium microporous zirconium silicate compositions for the treatment of hyperkalemia in patients also suffering from hypercalcemia.

36 Claims, 19 Drawing Sheets

Dark = ZrO3 (oct), Light = SiO2 (tet), Cations not shown

(51) Int. Cl.
*A61K 9/14* (2006.01)
*C07F 7/02* (2006.01)
*C01B 39/00* (2006.01)
*B01J 19/00* (2006.01)
*B01J 19/18* (2006.01)
*B01J 39/02* (2006.01)
*B01J 39/14* (2006.01)

(52) U.S. Cl.
CPC ....... *B01J 19/0013* (2013.01); *B01J 19/0066* (2013.01); *B01J 19/18* (2013.01); *B01J 39/02* (2013.01); *B01J 39/14* (2013.01); *C01B 39/00* (2013.01); *C07F 7/025* (2013.01); *B01J 2219/00063* (2013.01); *B01J 2219/00094* (2013.01); *B01J 2219/00768* (2013.01)

(58) Field of Classification Search
CPC .............. C01P 2002/82; C01P 2004/52; C01P 2004/61; C07F 7/025; C01B 33/20; C01B 39/00; C01B 39/02; C01B 39/46
See application file for complete search history.

(56) References Cited

U.S. PATENT DOCUMENTS

| | | |
|---|---|---|
| 4,581,141 A | 4/1986 | Ash |
| 4,943,545 A | 7/1990 | Chang et al. |
| 5,015,453 A | 5/1991 | Chapman |
| 5,338,527 A | 8/1994 | Lambert |
| 5,518,707 A | 5/1996 | Bedard et al. |
| 5,624,652 A | 4/1997 | Aldcroft et al. |
| 5,888,472 A | 3/1999 | Bem et al. |
| 5,891,417 A | 4/1999 | Bem et al. |
| 5,910,299 A | 6/1999 | Carluccio et al. |
| 6,007,790 A | 12/1999 | Bedard et al. |
| 6,099,737 A | 8/2000 | Sherman et al. |
| 6,146,613 A | 11/2000 | Anglerot et al. |
| 6,159,505 A | 12/2000 | Piper |
| 6,332,985 B1 | 12/2001 | Sherman et al. |
| 6,379,641 B1 | 4/2002 | Bedard et al. |
| 6,579,460 B1 | 6/2003 | Willis et al. |
| 6,596,254 B1 | 7/2003 | Nenoff et al. |
| 6,689,335 B1 | 2/2004 | Bringley et al. |
| 6,814,871 B1 | 11/2004 | Bem et al. |
| 7,297,319 B2 | 11/2007 | Vitale-Rojas et al. |
| 7,488,495 B2 | 2/2009 | Charmot et al. |
| 7,566,432 B2 | 7/2009 | Wong |
| 7,854,924 B2 | 12/2010 | Alpern et al. |
| 7,967,984 B2 | 6/2011 | Midorikawa et al. |
| 8,093,350 B2 | 1/2012 | Jung et al. |
| 8,192,758 B2 | 6/2012 | Charmot et al. |
| 8,282,960 B2 | 10/2012 | Charmot et al. |
| 8,431,502 B2 | 4/2013 | Dejneka et al. |
| 8,802,152 B2 | 8/2014 | Keyser et al. |
| 8,808,750 B2 | 8/2014 | Keyser et al. |
| 8,877,255 B2 | 11/2014 | Keyser et al. |
| 2004/0105895 A1 | 6/2004 | Ash |
| 2005/0220752 A1 | 10/2005 | Charmot et al. |
| 2007/0128424 A1 | 6/2007 | Omori et al. |
| 2007/0202180 A1 | 8/2007 | Liversidge et al. |
| 2007/0269499 A1 | 11/2007 | Hen et al. |
| 2008/0241092 A1 | 10/2008 | Charmot et al. |
| 2009/0155370 A1 | 6/2009 | Cope et al. |
| 2009/0186093 A1 | 7/2009 | Liu et al. |
| 2009/0263478 A1 | 10/2009 | Arnold et al. |
| 2010/0104527 A1 | 4/2010 | Mansky et al. |
| 2010/0322847 A1 | 12/2010 | Xiao et al. |
| 2011/0097401 A1 | 4/2011 | Phillips et al. |
| 2012/0070468 A1 | 3/2012 | Bedard et al. |
| 2012/0213847 A1 | 8/2012 | Keyser et al. |
| 2012/0259141 A1 | 10/2012 | Yilmaz et al. |
| 2012/0289931 A1 | 11/2012 | Robinson et al. |
| 2013/0123096 A1 | 5/2013 | Xiao et al. |
| 2013/0129611 A1 | 5/2013 | Maurer et al. |
| 2013/0202524 A1 | 8/2013 | Maurer et al. |
| 2013/0259949 A1 | 10/2013 | Cope et al. |
| 2013/0296159 A1 | 11/2013 | Feyen et al. |
| 2014/0044804 A1 | 2/2014 | Cope et al. |

FOREIGN PATENT DOCUMENTS

| | | |
|---|---|---|
| EP | 0451958 | 10/1991 |
| EP | 0832897 A2 | 4/1998 |
| EP | 1038580 | 3/1999 |
| EP | 0982785 | 3/2000 |
| ES | 2304890 | 10/2008 |
| GB | 2038301 | 7/1980 |
| WO | 02062356 | 8/2002 |
| WO | 2005053650 A1 | 6/2005 |
| WO | 2007100466 | 11/2007 |
| WO | 2010022381 | 2/2010 |
| WO | 2012109590 A2 | 8/2012 |
| WO | WO 2014/011876 A2 | 1/2014 |

OTHER PUBLICATIONS

International Search Report and Written Opinion of PCT/US2014/064542 mailed Jan. 27, 2015.
International Search Report and Written Opinion of PCT/US2014/064548 mailed Jan. 27, 2015.
International Search Report and Written Opinion of PCT/US2014/69524 mailed Mar. 3, 2015.
Timmer et al., Journal of the American Society of Nephrology (1999) vol. 10, pp. 666-674.
Stephen R. Ash, "Sorbents in Treatment of Uremia: A Short History and a Great Future," Seminars in Dialysis, vol. 22, No. 6 (Nov.-Dec. 2009), pp. 615-622.
Stephen R. Ash, Cation Exchangers as Oral Sorbents for Ammonium and Potassium: PSS, ZP and ZS (Zirconium Silicate), Clarian Arnett Health, Wellbound and HemoCleanse Inc., Lafayette, IN, (2007), ASAIO Innovation Conference, Chicago (25 pages).
Baussy et al., Bull. Soc. fr. Mineral. Cristallogr. (1974) vol. 97, pp. 433-444.
David S. Bem et al., "Synthesis and Characterization of a New Family of Microporous Zirconium Silicates," (1999), Materials Research Society, Symposium Procedures, vol. 549, pp. 73-78.
Bortun et al., Chem. Mater. (1997) vol. 9, No. 8, pp. 1854-1864.
Rich Braun et al., "Ammonium Removal With a Novel Zirconium Silicate," Presentation, (2001), ASAIO Conference (16 pages).
Chukanov et al., Russian Journal of Physical Chemistry B (2011) vol. 5, No. 2, pp. 278-283.
Chukanov et al., Russian Journal of Physical Chemistry B (2011) vol. 5, No. 2, pp. 284-289.
Chukanov et al., Minerals as Advanced Materials II (2012) pp. 167-179 (S.V. Krivovichev (ed)).
Clearfield et al., Journal of Molecular Structure (1998) vol. 470, pp. 207-213.
Dunn et al., American Mineralogist (1977) vol. 62, pp. 416-420.
Ferreira et al., Chem. Mater. (2001) vol. 13, pp. 355-363.
Ferreira et al., Inorganica Chimica Acta (2003) vol. 356, pp. 19-26.
Ferreira et al., Journal of Solid State Chemistry (2010) vol. 183, pp. 3067-3072.
Fewox et al., J. Phys. Chem. A (2008) vol. 112, pp. 2589-2597.
Fundamental of Physics © 1997 John Wiley & Sons, Inc., USA, pp. 947-949, section 37-9 X-Ray Diffraction.
Henderson, Lee W., Seminars in Dialysis (2012) vol. 25, No. 3, pp. 320-325.
International Search Report and Written Opinion of PCT/US2012/024727 mailed Aug. 7, 2012.
International Search Report and Written Opinion of PCT/US2013/066207 mailed Feb. 14, 2014.
International Search Report and Written Opinion of PCT/US2013/045219 mailed Nov. 8, 2013.
Lopes et al., Quim. Nova. (2008) vol. 31, No. 2, pp. 321-325.
Navascues et al., Desalination (2006) vol. 199, pp. 368-370.
Navascues et al., Chemical Engineering and Processing (2008) vol. 47, pp. 1139-1149.

(56) References Cited

OTHER PUBLICATIONS

Pekov et al., Cryst. Report (2010) vol. 55, No. 6, pp. 1031-1040.
Pertierra et al., Inorganic Chemistry Comm. (2002) vol. 5, pp. 824-828.
Poojary et al., Inorg. Chem. (1997) vol. 36, pp. 3072-3079.
Rocha et al., Chem. Comm. (1998) 1269-1270.
Yong-Nan et al., Chem. Res. Chinese U. (2002) vol. 18, No. 4, pp. 380-384.
ZS-9 Particle Size Distribution Analysis Report (4 pages), Nov. 4, 2009.
ZS Pharma Products website from Sep. 9, 2010 (http://web.archive.org/web/20100906160415/http://zspharma.com/products, accessed Mar. 28, 2014 via archive.org).
ZS Pharma Welcome website Sep. 6, 2010 (http://web.archive.org/web/20100906213849/http://zspharma.com/index.php?format=feed&type=atom, accessed Mar. 28, 2014 via archive.org) containing a comment from Dan Olson from Jan. 9, 2010.
International Search Report and Written Opinion of PCT/US2014/032815 mailed Nov. 6, 2014.
Roswell et al., "Metal-organic Frameworks: A New Class of Porous Materials," Microporous and Mesoporous Materials (2004) vol. 73, pp. 3-14.
"Award Honors High-Tech Pharmaceutical Company", The Forth Worth Chamberletter, retrieved from: http://www.fortworthchamber/com/chamber/letter/award-honors-high-tech-pharmaceutical-company/, 2011.
"Safety & Efficacy of Zirconium Silicate in Chronic Kidney Disease or Moderate Kidney Dysfunction with Mild Hyperkalemia", ClinicalTrials.gov, retrieved from: https://clinicaltrials.gov/ct2/show/NCT01493024, 2011.
"Safety & Efficacy of Zirconium Silicate in Mild to Moderate Hyperkalemia", ClinicalTrials.gov, retrieved from: https://clinicaltrials.gov/ct2/show/record/NCT01737697, 2012.
"Welcome to ZS Pharma", retrieved from: http://web.archive.org/web/20100905040319/http://zspharma.com/, 2010.
Office Action issued in Chilean Patent Application No. 78-2015 dated Sep. 29, 2016.

Dark = ZrO3 (oct), Light = SiO2 (tet), Cations not shown

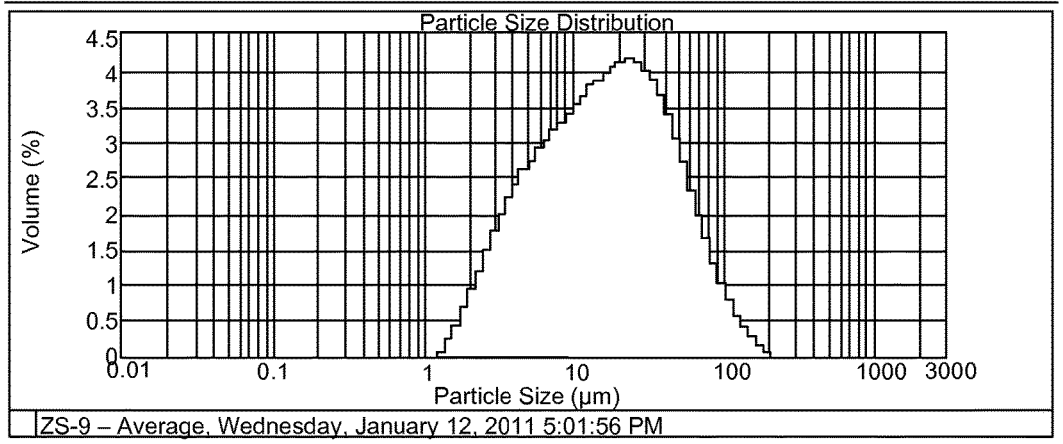
Fig. 2 (ZS-9 lot 5332-04310-A)

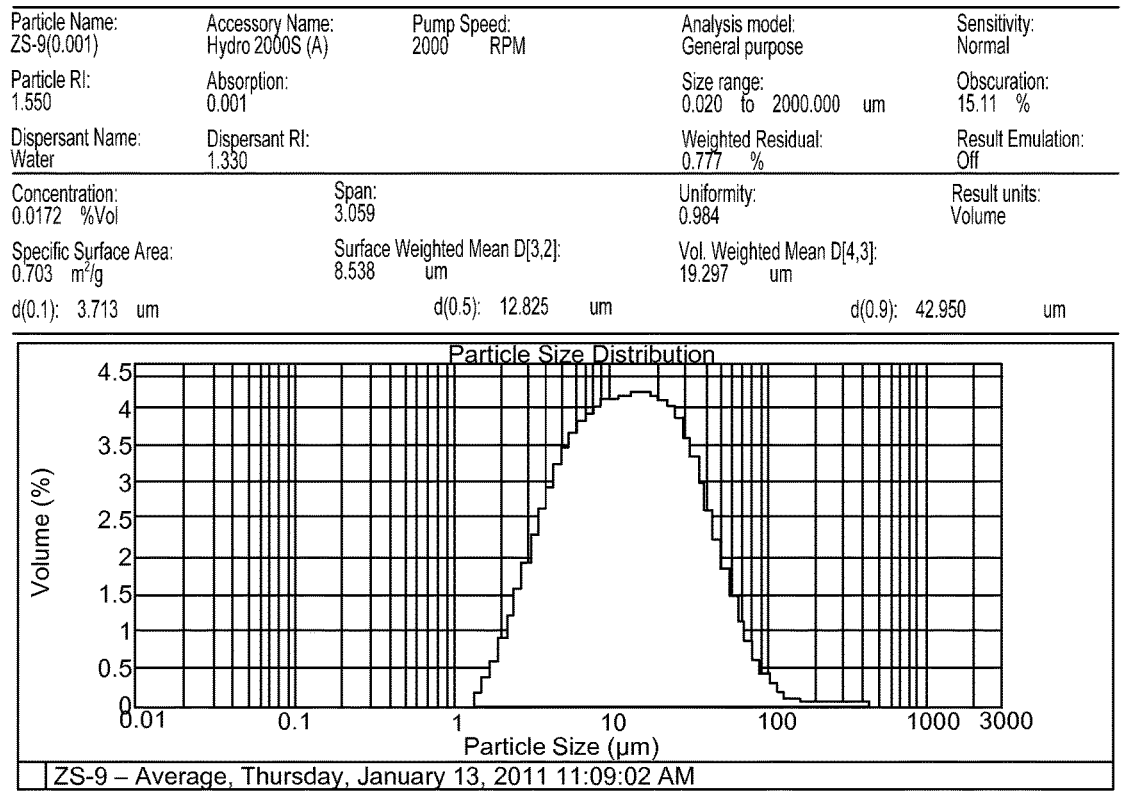
Fig. 3 (ZS-9 lot 5332-05410-A)

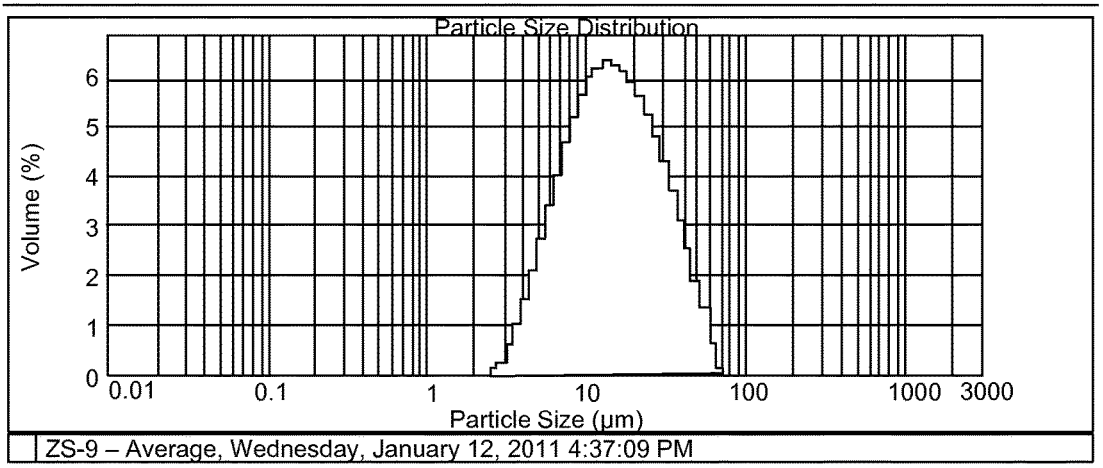
Fig. 4 (ZS-9 preclinical lot)

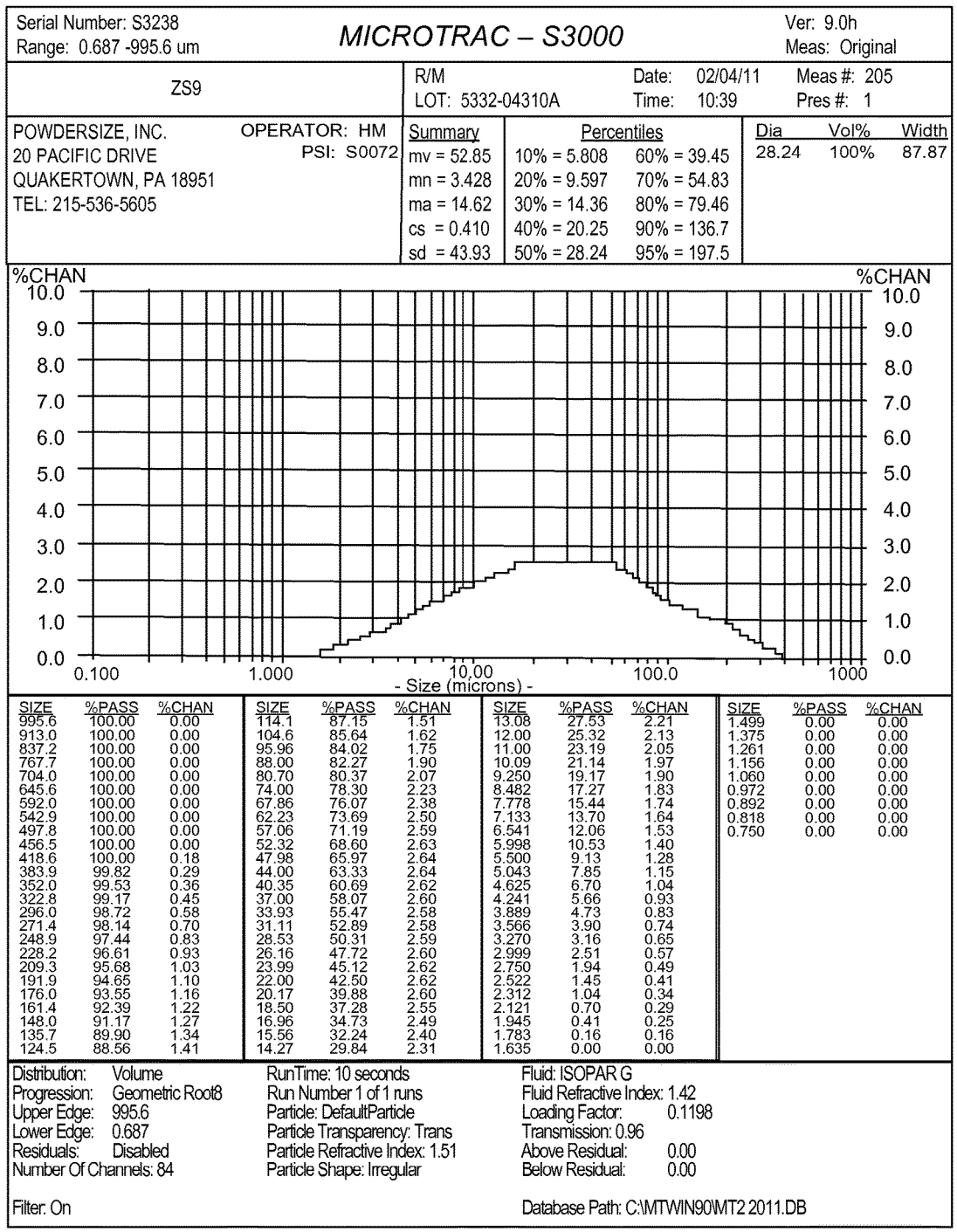
Fig. 5: (lot 5332-04310A w/o screening)

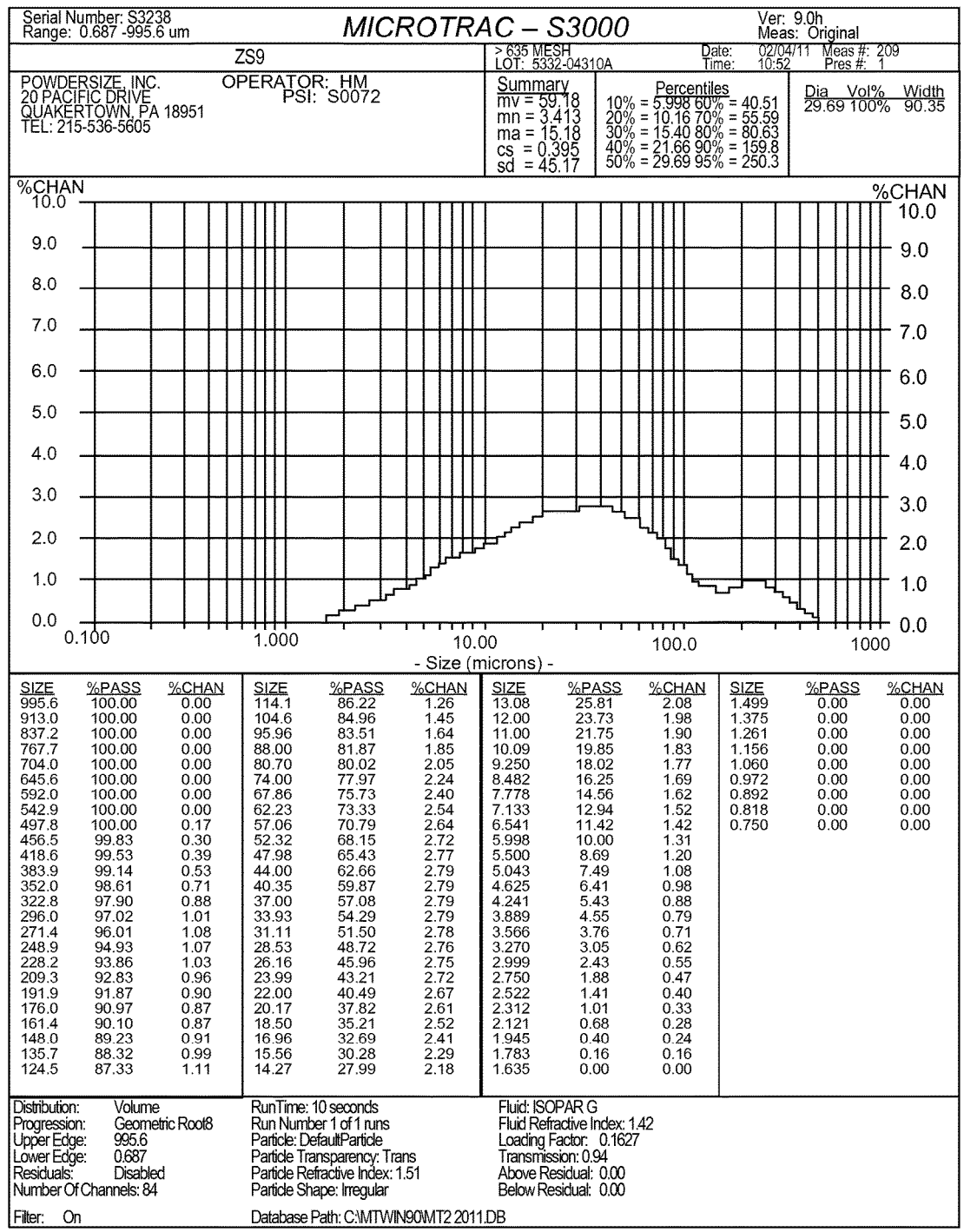
Fig. 6: (lot 5332-04310A 635 mesh)

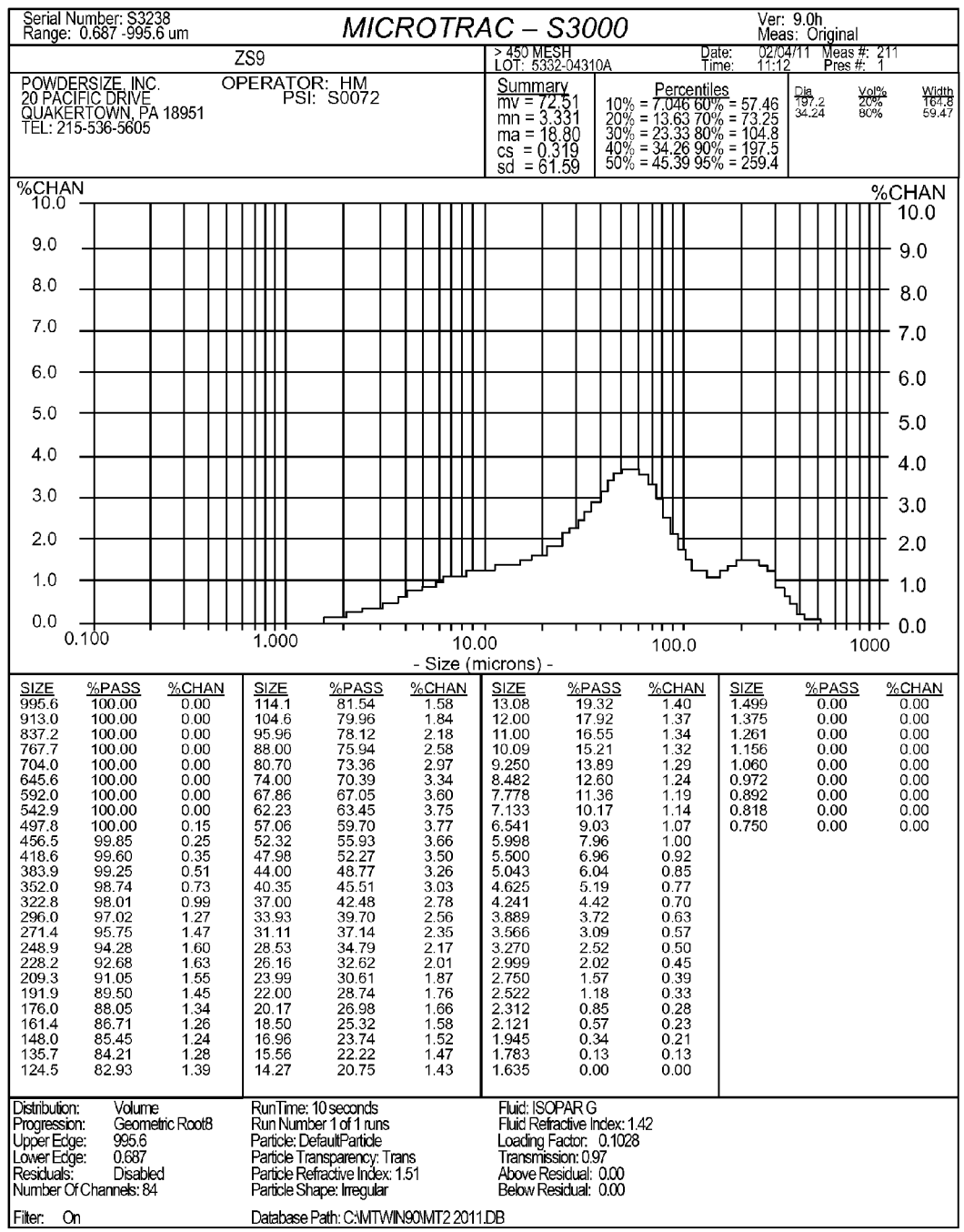
Fig. 7: (lot 5332-04310A 450 mesh)

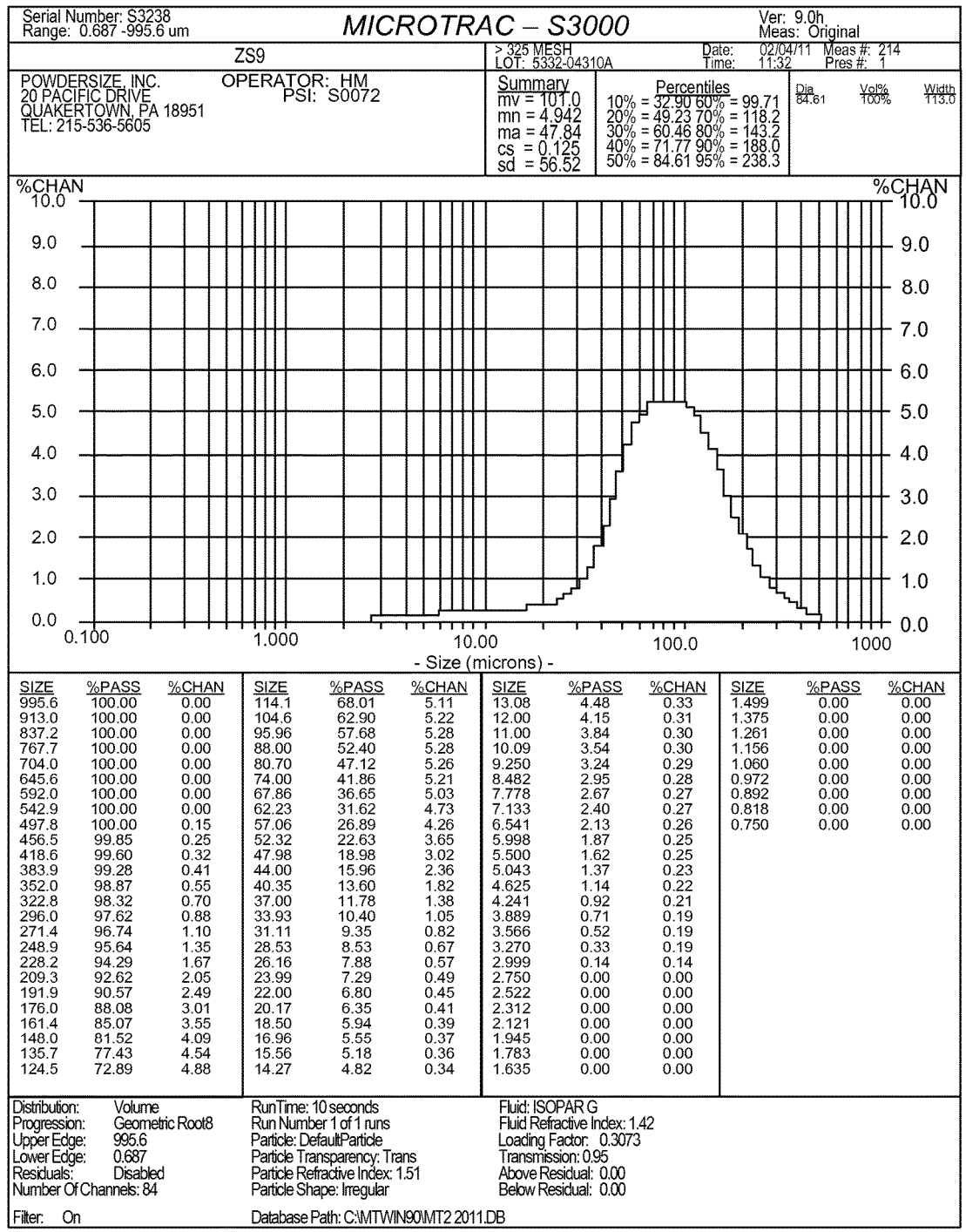
Fig. 8: (lot 5332-04310A 325 mesh)

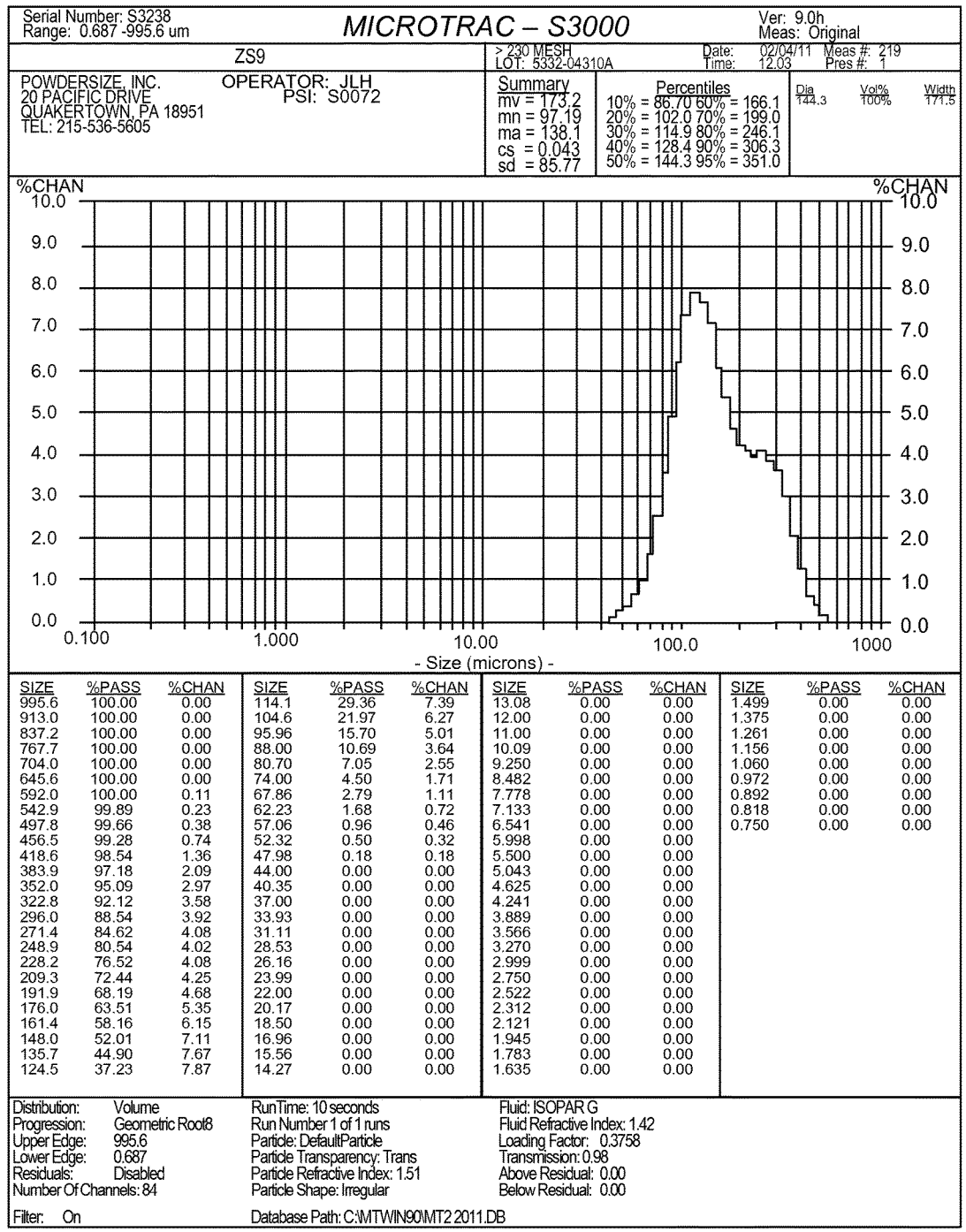
Fig. 9: (lot 5332-04310A 230 mesh)

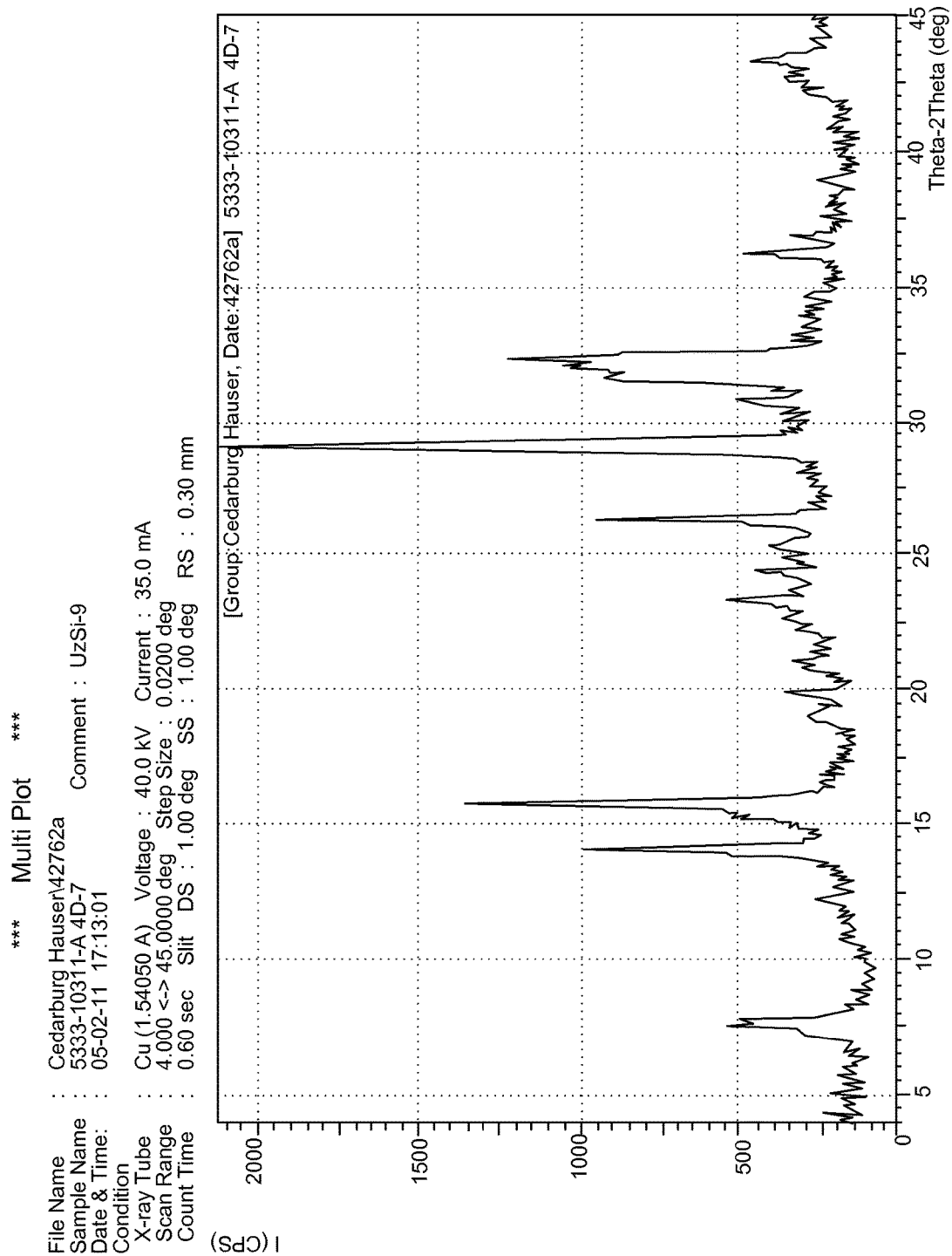
Fig. 10: XRD plot for ZS-9 prepared in accordance with Example 12.

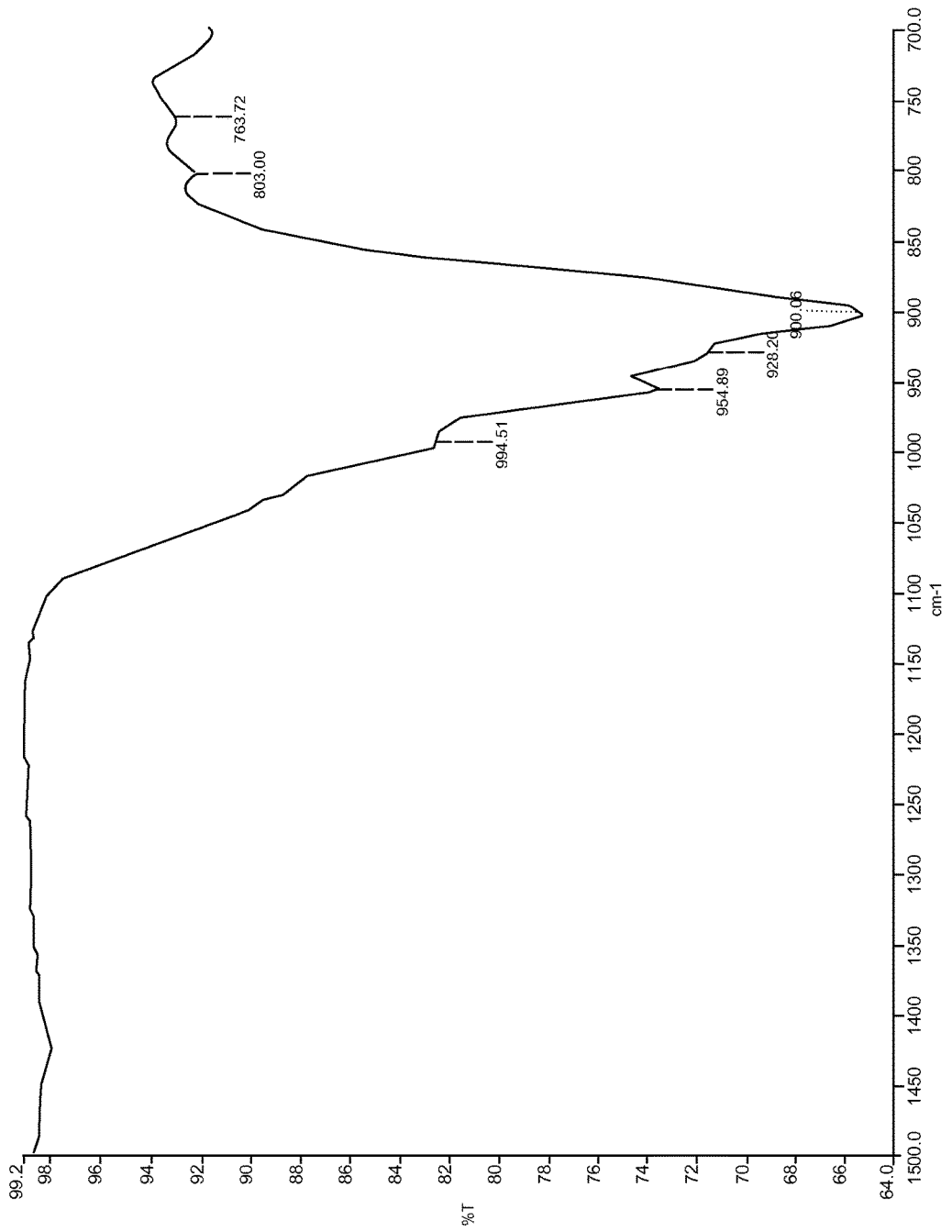
Fig. 11: FTIR plot for ZS-9 prepared in accordance with Example 12

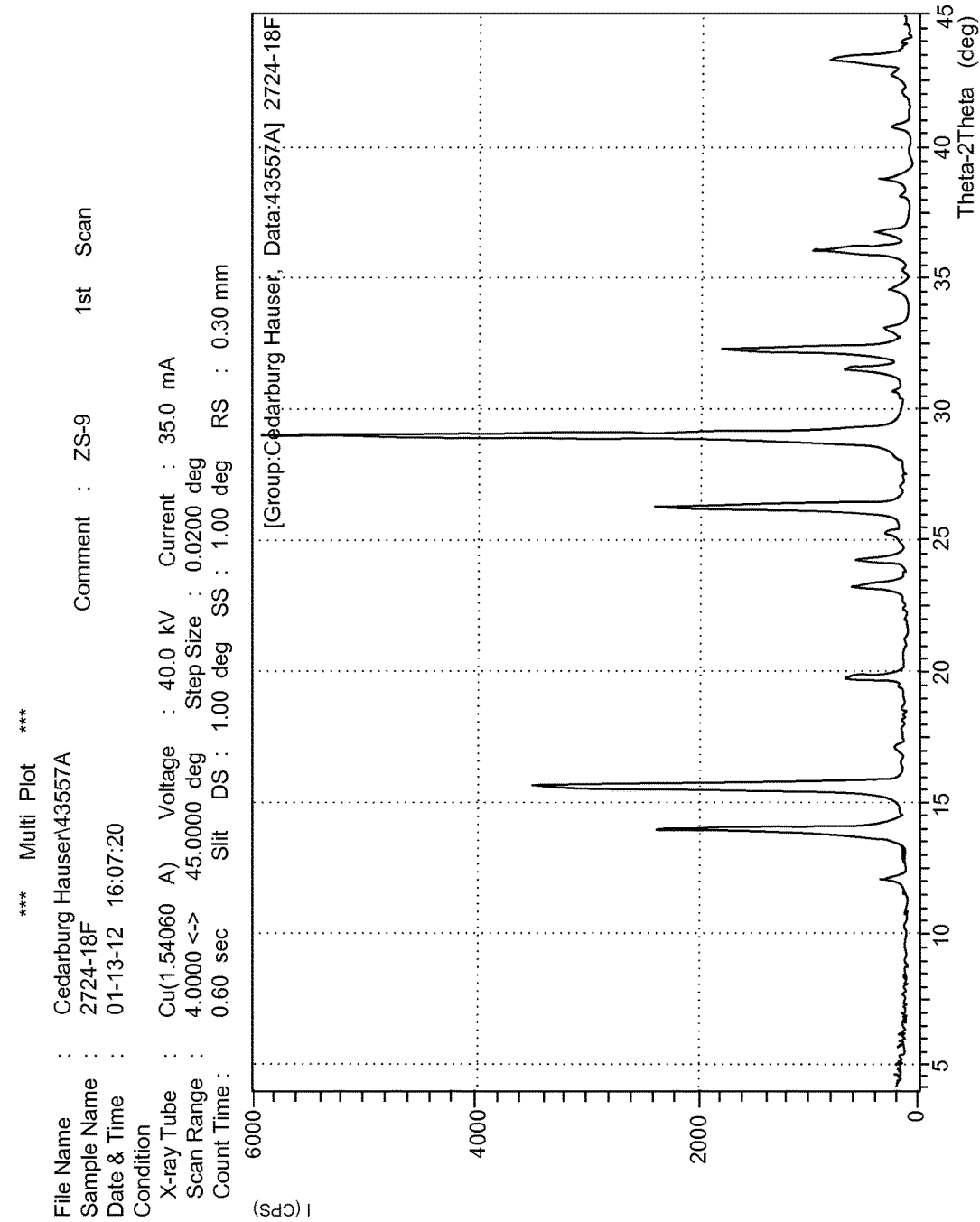
Fig. 12: XRD plot for ZS-9 prepared in accordance with Example 13.

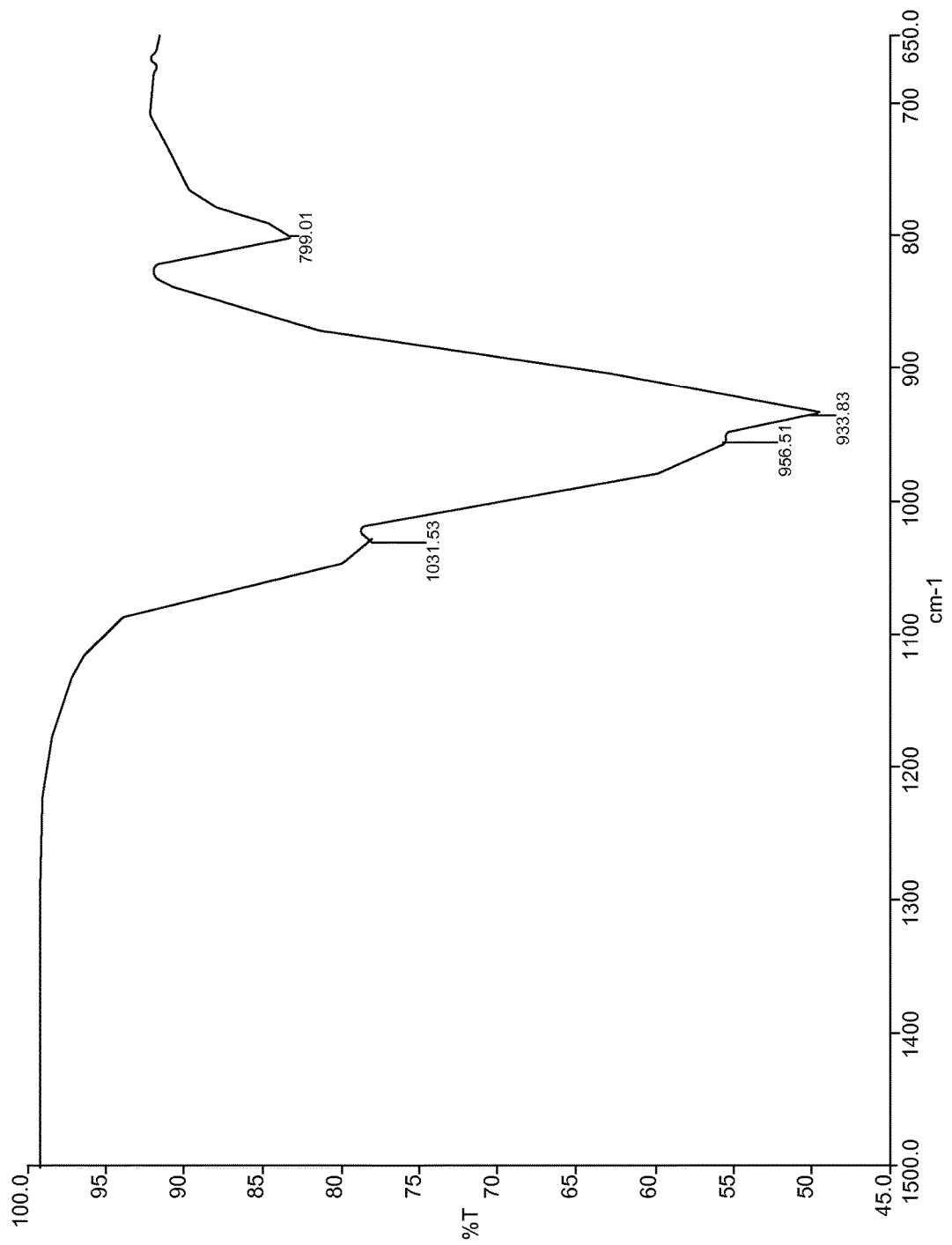
Fig. 13: FTIR plot for ZS-9 prepared in accordance with Example 13.

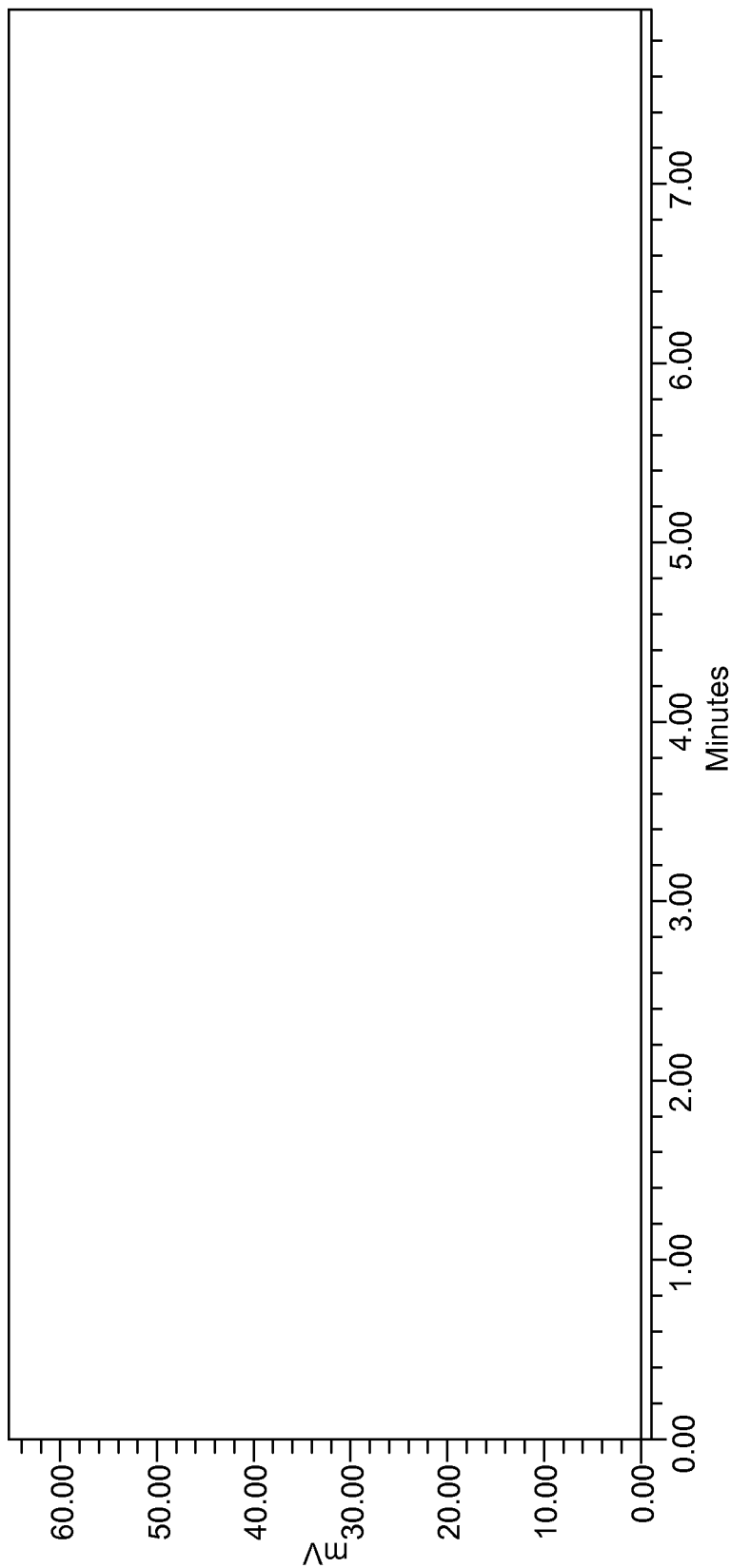
Fig. 14: Example of the Blank Solution Chromatogram

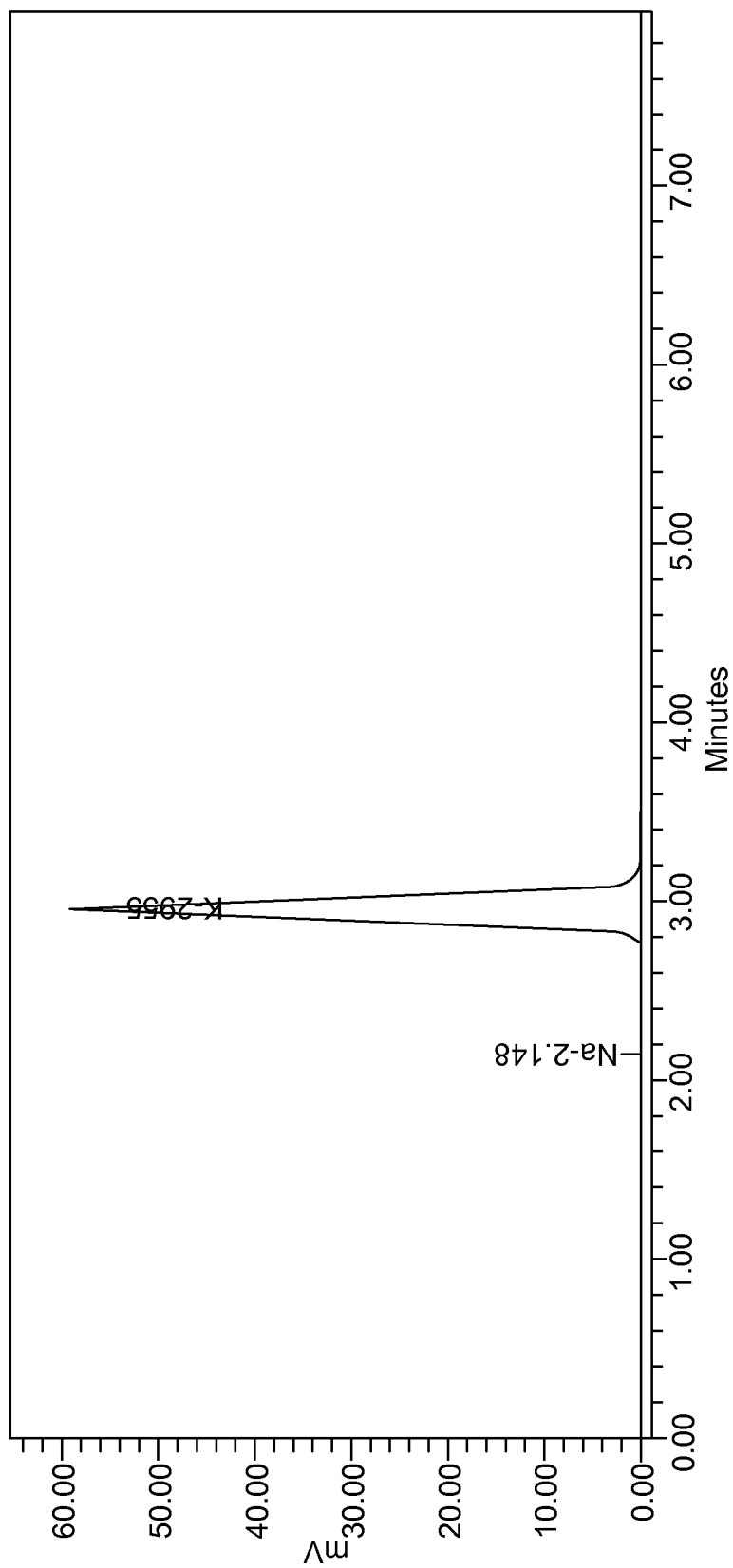
Fig. 15: Example of the Assay Standard Solution Chromatogram.

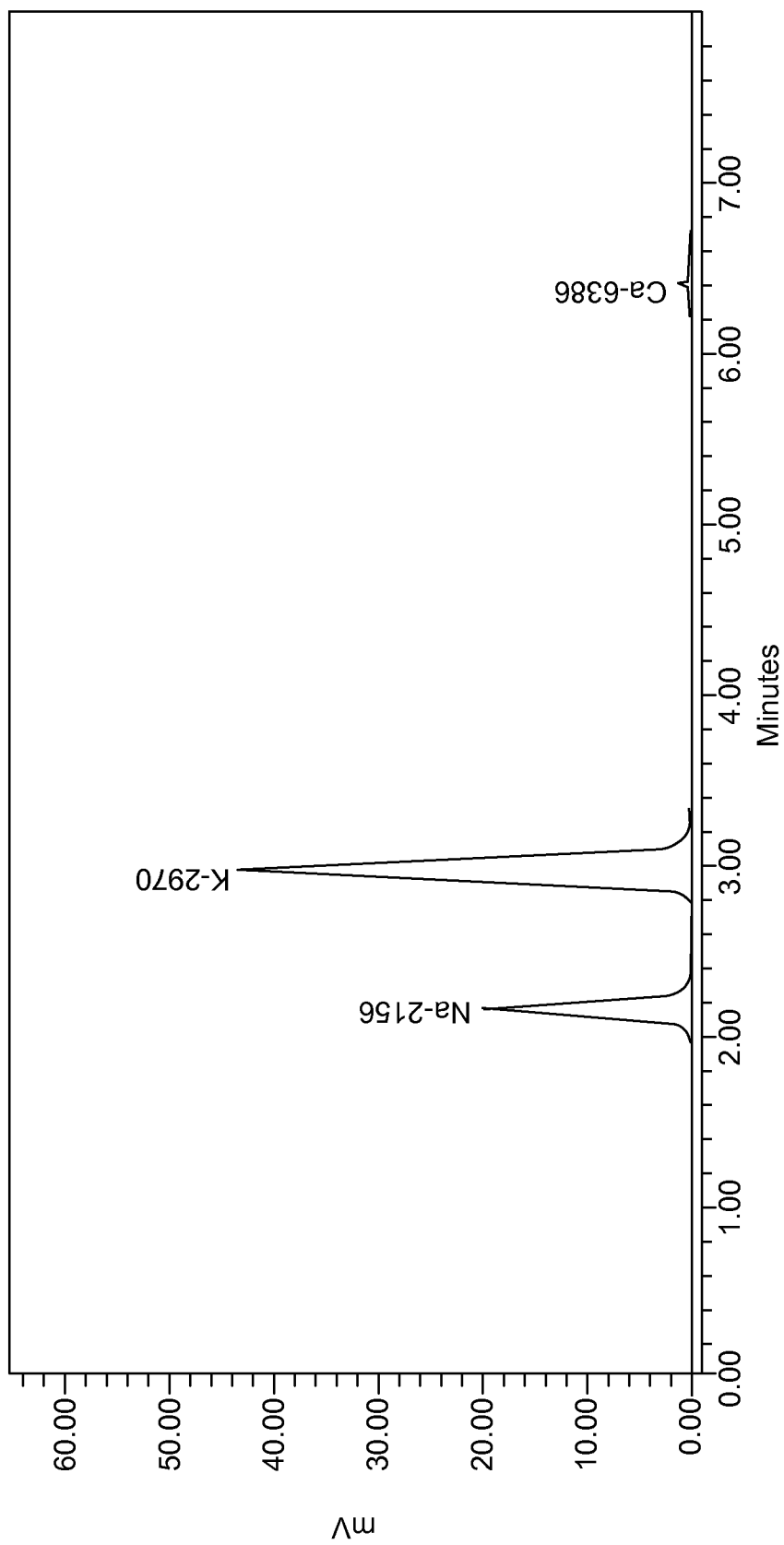
Fig. 16: Exemplary Sample Chromatogram.

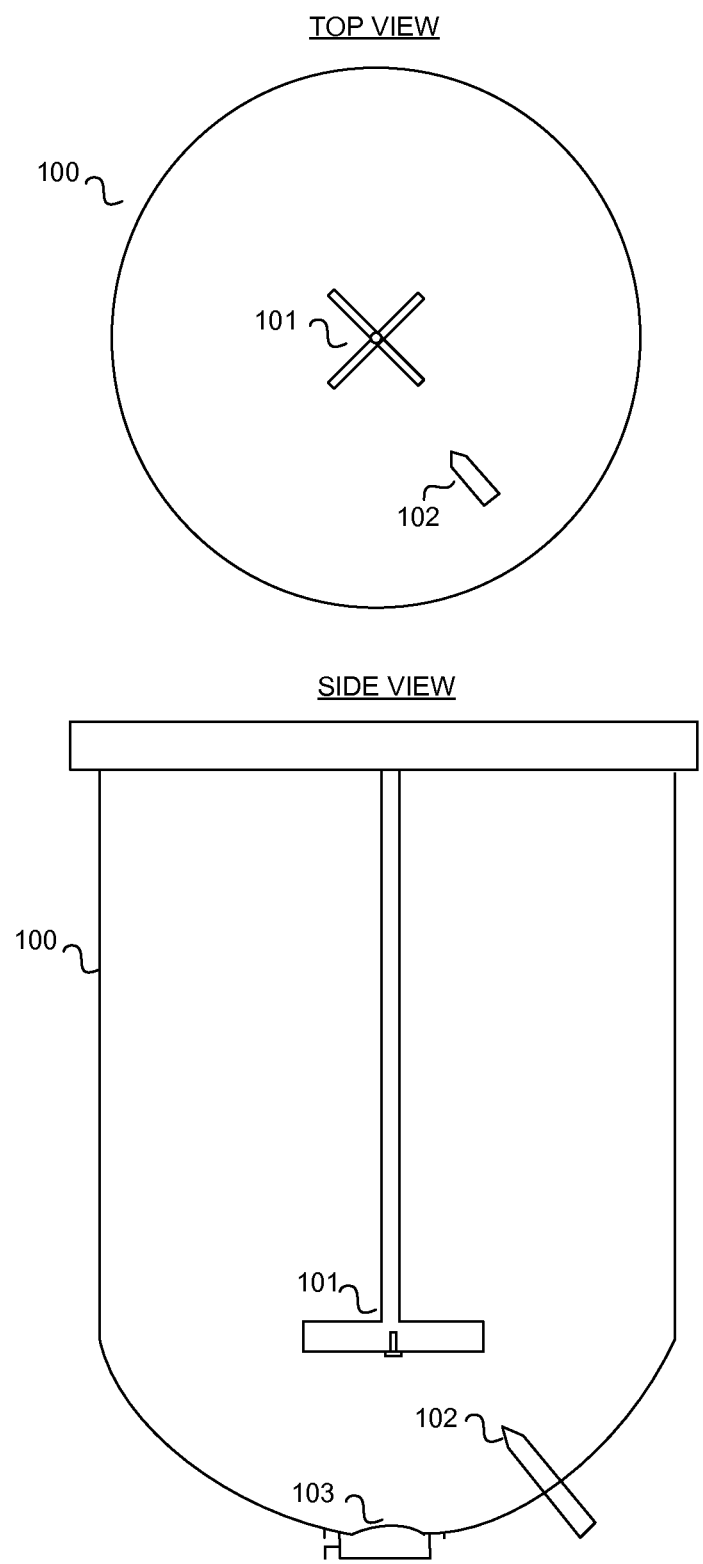
Fig. 17: 200-L reaction vessel with standard agitator arrangement.

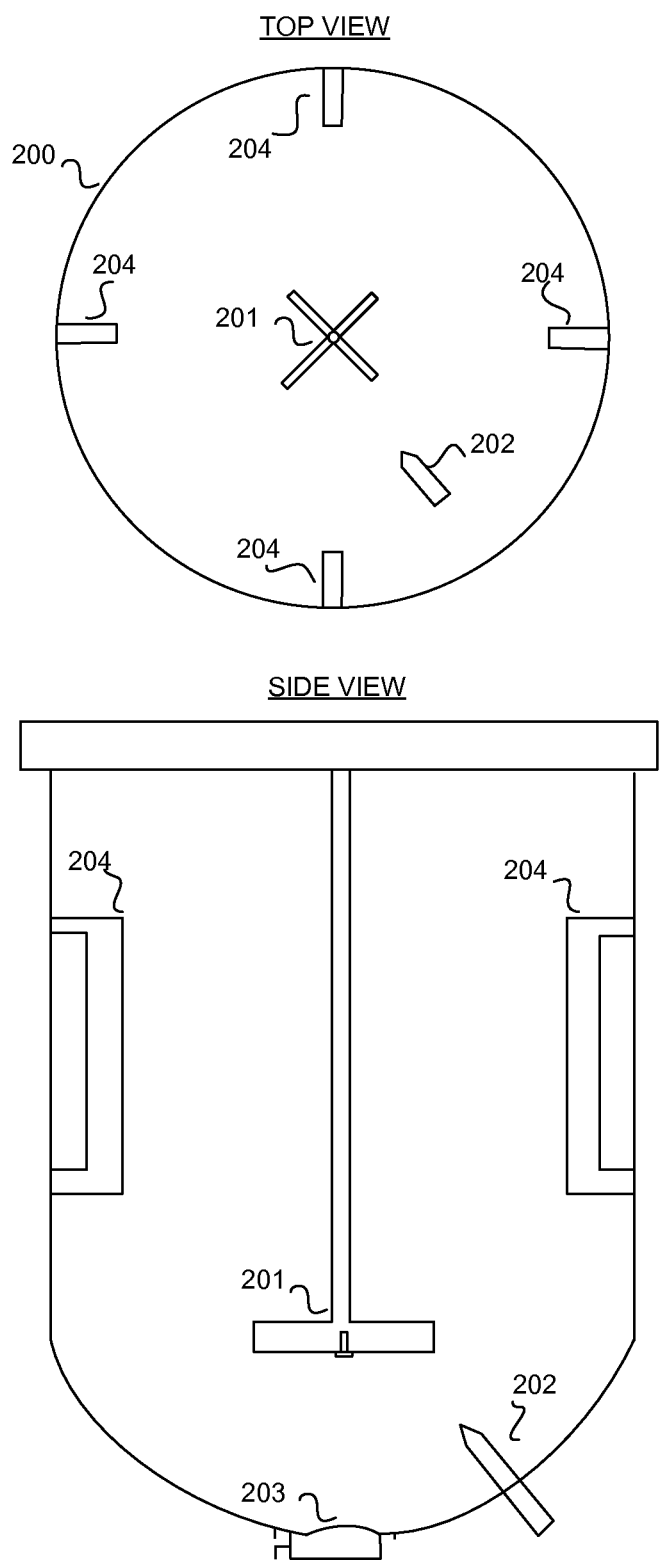
Fig. 18: 200-L reaction vessel with baffles for production of enhanced ZS-9

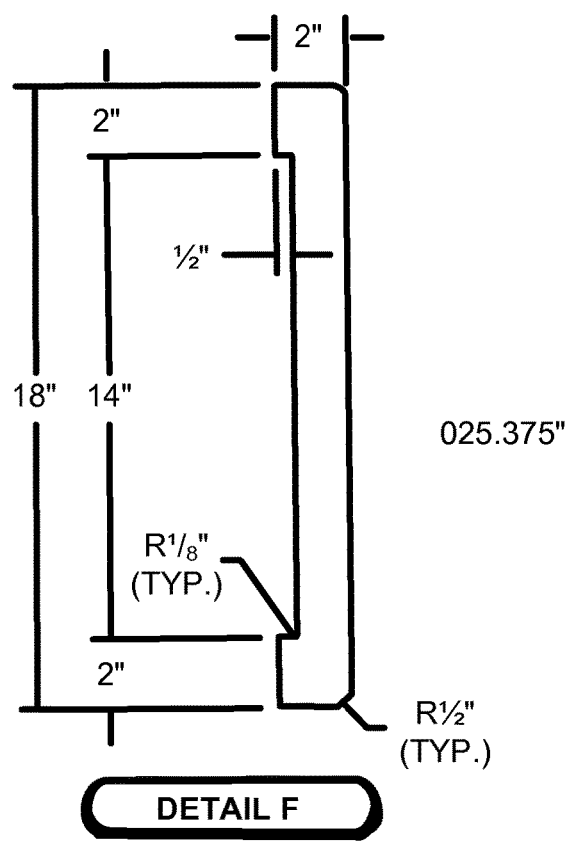
Fig. 19: Detail of baffle design for 200-L reaction vessel for production of enhanced ZS-9

MICROPOROUS ZIRCONIUM SILICATE FOR THE TREATMENT OF HYPERKALEMIA IN HYPERCALCEMIC PATIENTS AND IMPROVED CALCIUM-CONTAINING COMPOSITIONS FOR THE TREATMENT OF HYPERKALEMIA

RELATED APPLICATIONS

The present application claims benefit from U.S. Provisional Patent Application Ser. No. 61/670,415 filed Jul. 11, 2012 and U.S. Provisional Patent Application Ser. No. 61/800,291 filed Mar. 15, 2013, the contents of which are incorporated herein by reference, in their entireties.

BACKGROUND OF THE INVENTION (i) Field of the Invention

The present invention relates to novel microporous zirconium silicate ("ZS") compositions that are formulated to remove toxins, e.g., potassium ions or ammonium ions, from the gastrointestinal tract at an elevated rate while avoiding the removal of calcium. The preferred compositions of the present invention also avoid certain undesirable side effects including potential entry of particles into the bloodstream and potential increase in pH of urine in patients. These compositions are particularly useful in the therapeutic treatment of hyperkalemia. Also disclosed are microporous ZS compositions having enhanced purity and potassium exchange capacity (KEC), and methods for making such microporous ZS compositions. Further, the present invention relates to the use of microporous ZS compositions to remove calcium from hypercalcemic patients as well as toxins such as potassium or ammonium ions.

(ii) Description of the Related Art

Acute hyperkalemia is a serious life threatening condition resulting from elevated serum potassium levels. Potassium is a ubiquitous ion, involved in numerous processes in the human body. It is the most abundant intracellular cation and is critically important for numerous physiological processes, including maintenance of cellular membrane potential, homeostasis of cell volume, and transmission of action potentials. Its main dietary sources are vegetables (tomatoes and potatoes), fruit (oranges, bananas) and meat. The normal potassium levels in plasma are between 3.5-5.0 mmol/l with the kidney being the main regulator of potassium levels. The renal elimination of potassium is passive (through the glomeruli) with active reabsorption in the proximal tubule and the ascending limb of the loop of Henle. There is active excretion of potassium in the distal tubules and the collecting duct, both of these processes are controlled by aldosterone.

Increased extracellular potassium levels result in depolarization of the membrane potential of cells. This depolarization opens some voltage-gated sodium channels, but not enough to generate an action potential. After a short period of time, the open sodium channels inactivate and become refractory, increasing the threshold to generate an action potential. This leads to impairment of the neuromuscular-, cardiac- and gastrointestinal organ systems, and this impairment is responsible for the symptoms seen with hyperkalemia. Of greatest concern is the effect on the cardiac system, where impairment of cardiac conduction can lead to fatal cardiac arrhythmias such as asystole or ventricular fibrillation. Because of the potential for fatal cardiac arrhythmias, hyperkalemia represents an acute metabolic emergency that must be immediately corrected.

Hyperkalemia may develop when there is excessive production of serum potassium (oral intake, tissue breakdown). Ineffective elimination, which is the most common cause of hyperkalemia, can be hormonal (as in aldosterone deficiency), pharmacologic (treatment with ACE-inhibitors or angiotensin-receptor blockers) or, more commonly, due to reduced kidney function or advanced cardiac failure. The most common cause of hyperkalemia is renal insufficiency, and there is a close correlation between degree of kidney failure and serum potassium (S-K) levels. In addition, a number of different commonly used drugs cause hyperkalemia, such as ACE-inhibitors, angiotensin receptor blockers, potassium-sparing diuretics (e.g. amiloride), NSAIDs (such as ibuprofen, naproxen, celecoxib), heparin and certain cytotoxic and/or antibiotic drugs (such as cyclosporin and trimethoprim). Finally, beta-receptor blocking agents, digoxin or succinylcholine are other well-known causes of hyperkalemia. In addition, advanced degrees of congestive heart disease, massive injuries, burns or intravascular hemolysis cause hyperkalemia, as can metabolic acidosis, most often as part of diabetic ketoacidosis.

Symptoms of hyperkalemia are somewhat non-specific and generally include malaise, palpitations and muscle weakness or signs of cardiac arrhythmias, such as palpitations, brady-tachycardia or dizziness/fainting. Often, however, the hyperkalemia is detected during routine screening blood tests for a medical disorder or after severe complications have developed, such as cardiac arrhythmias or sudden death. Diagnosis is obviously established by S-K measurements.

Treatment depends on the S-K levels. In milder cases (S-K between 5-6.5 mmol/l), acute treatment with a potassium binding resin (Kayexalate®), combined with dietary advice (low potassium diet) and possibly modification of drug treatment (if treated with drugs causing hyperkalemia) is the standard of care; if S-K is above 6.5 mmol/l or if arrhythmias are present, emergency lowering of potassium and close monitoring in a hospital setting is mandated. The following treatments are typically used:

Kayexalate®, a resin that binds potassium in the intestine and hence increases fecal excretion, thereby reducing S-K levels. However, as Kayexalate® has been shown to cause intestinal obstruction and potential rupture. Further, diarrhea needs to be simultaneously induced with treatment. These factors have reduced the palatability of treatment with Kayexalate®.

Insulin IV (+glucose to prevent hypoglycemia), which shifts potassium into the cells and away from the blood.

Calcium supplementation. Calcium does not lower S-K, but it decreases myocardial excitability and hence stabilizes the myocardium, reducing the risk for cardiac arrhythmias.

Bicarbonate. The bicarbonate ion will stimulate an exchange of K+ for Na+, thus leading to stimulation of the sodium-potassium ATPase.

Dialysis (in severe cases).

The only commercial pharmacologic modality that actually increases elimination of potassium from the body is Kayexalate®; however, due to the need to induce diarrhea, Kayexalate® cannot be administered on a chronic basis, and even in the acute setting, with the accompanying need to induce diarrhea, combined with only marginal efficacy and a foul smell and taste, reduces its usefulness.

The use of ZS or titanium silicate microporous ion exchangers to remove toxic cations and anions from blood or dialysate is described in U.S. Pat. Nos. 6,579,460, 6,099,737, and 6,332,985, each of which is incorporated herein in their entirety. Additional examples of microporous ion exchangers are found in U.S. Pat. Nos. 6,814,871, 5,891,417, and 5,888,472, each of which is incorporated herein in their entirety.

In U.S. patent application Ser. No. 13/371,080 (the '080 application), filed Feb. 10, 2012, the contents of which are incorporated herein, the present inventors disclosed that known ZS compositions may exhibit undesirable effects when utilized in vivo for the removal of potassium in the treatment of hyperkalemia. Specifically, the administration of ZS molecular sieve compositions has been associated with an incidence of mixed leukocyte inflammation, minimal acute urinary bladder inflammation and the observation of unidentified crystals in the renal pelvis and urine in animal studies, as well as an increase in urine pH. Further, known ZS compositions have had issues with crystalline impurities and undesirably low cation exchange capacity. The '080 application discloses novel ZS molecular sieves to address the problem associated with existing hyperkalemia treatments, and novel methods of treatment for hyperkalemia utilizing these novel compositions. In U.S. Provisional Patent Application No. 61/658,117 (the '117 application), the contents of which are incorporated herein, the present inventors disclosed novel ZS products and methods of manufacturing.

The present inventors have now discovered that treatment of hyperkalemia with the ZS compositions disclosed in the '080 and '117 applications is accompanied by a withdrawal of significant amounts of calcium from the patient's body.

SUMMARY OF THE EMBODIMENTS OF THE INVENTION

ZS and zirconium germanate molecular sieves have a microporous structure composed of $ZrO_3$ octahedral units and at least one $SiO_2$ tetrahedral units and $GeO_2$ tetrahedral units. These molecular sieves have the empirical formula:

$$A_pM_xZr_{1-x}Si_nGe_yO_m \qquad (I)$$

where A is an exchangeable cation selected from potassium ion, sodium ion, rubidium ion, cesium ion, calcium ion, magnesium ion, hydronium ion or mixtures thereof, M is at least one framework metal selected from the group consisting of hafnium (4+), tin (4+), niobium (5+), titanium (4+), cerium (4+), germanium (4+), praseodymium (4+), and terbium (4+), "p" has a value from about 1 to about 20, "x" has a value from 0 to less than 1, "n" has a value from about 0 to about 12, "y" has a value from 0 to about 12, "m" has a value from about 3 to about 36 and 1≤n+y≤12. The germanium can substitute for the silicon, zirconium or combinations thereof. Since the compositions are essentially insoluble in bodily fluids (at neutral or basic pH), they can be orally ingested in order to remove toxins in the gastrointestinal system. The compositions of the present invention comprise an elevated level of calcium that allows the compositions to treat hyperkalemia without withdrawing calcium from the patient's body or without withdrawing undesirable amounts of calcium from the patient's body. Preferably, the ZS compositions comprise calcium levels ranging from 1 to 100 ppm, preferably from 1 to 30 ppm, and more preferably between 5 and 25 ppm. The compositions of the present invention preferably have a calcium content that is sufficient to avoid absorption of significant amounts of calcium from the patient's body while maintaining high potassium exchange capacity.

Without being bound by any particular mechanistic theory, the absorption of the calcium onto the ZS composition allows for the removal of excess potassium from a patient's body without the withdrawal of calcium. Accordingly, any divalent cation may be absorbed onto the ZS composition to lessen the interaction and absorption of calcium with the composition. As such, in one embodiment, the calcium may be substituted by any divalent cation. In one embodiment, the divalent cation may be selected from any of the elements found in group 2 of the periodic table or alkaline earth metals. In another embodiment, the divalent cation is preferably selected from calcium or magnesium. The divalent cation will be present in an amount effective to lessen the withdrawal of the calcium from a patient suffering from hyperkalemia. In one embodiment, a single type of divalent cation or a mixture of various types of divalent cations may be absorbed onto the ZS composition. In an one embodiment, the ZS composition may comprise elevated levels of magnesium. The ZS compositions comprise magnesium in levels ranging from 1 to 100 ppm, preferably from 1 to 30 ppm, and more preferably from 5 to 25 ppm. In another embodiment, the ZS compositions may comprise a mixture of both calcium and magnesium, where the ratio of calcium to magnesium ranges from 1:10 to 10:1, preferably form 1:5 to 5:1, more preferably from 1:2 to 2:1. Those of skill in the art will understand that the ratio of calcium to magnesium may be adjusted to any level to optimize the withdrawal of calcium from a hyperkalemic patient while at the same time having an optimal potassium exchange rate.

In one embodiment, the composition exhibits median particle size of greater than 3 microns and less than 7% of the particles in the composition have a diameter less than 3 microns. Preferably, less than 5% of the particles in the composition have a diameter less than 3 microns, more preferably less than 4% of the particles in the composition have a diameter less than 3 microns, more preferably less than 3% of the particles in the composition have a diameter of less than 3 microns, more preferably less than 2% of the particles in the composition have a diameter of less than 3 microns, more preferably less than 1% of the particles in the composition have a diameter of less than 3 microns, more preferably less than 0.5% of the particles in the composition have a diameter of less than 3 microns. Most preferably, none of the particles or only trace amounts have a diameter of less than 3 microns.

The median and average particle size is preferably greater than 3 microns and particles reaching a sizes on the order of 1,000 microns are possible for certain applications. Preferably, the median particle size ranges from 5 to 1000 microns, more preferably 10 to 600 microns, more preferably from 15 to 200 microns, and most preferably from 20 to 100 microns.

In one embodiment, the composition exhibiting the median particle size and fraction of particles in the composition having a diameter less than 3 micron described above also exhibits a sodium content of below 12% by weight. Preferably, the sodium contents is below 9% by weight, more preferably the sodium content is below 6% by weight, more preferably the sodium content is below 3% by weight, more preferably the sodium content is in a range of between 0.05 to 3% by weight, and most preferably 0.01% or less by weight or as low as possible.

In one embodiment, the invention involves a pharmaceutical product comprising the composition in capsule, powdered, or tablet form. In another embodiment of the invention, the pharmaceutical product is packaged in a kit in individual unit dosages sufficient to maintain a lowered serum potassium level. The dosage may range from approximately 1-60 grams per day or any whole number or integer interval therein. Such dosages can be individual capsules, tablets, or packaged powdered form of 1.25-20 grams of the ZS, preferably 2.5-15 grams of ZS, more preferably 5-10 grams of ZS. In another embodiment, the ZS may be a single unit dose of approximately 1.25-45 gram capsule, tablet or powdered package. In another embodiment, the product may be consumed once a day, three times daily, every other day, or weekly.

In one embodiment, a molecular sieve is provided which has an elevated cation exchange capacity, particularly potassium exchange capacity. The elevated cation exchange capacity is achieved by a specialized process and reactor configuration that lifts and more thoroughly suspends crystals throughout the reaction. In an embodiment of the invention, the ZS-9 crystals had a potassium exchange capacity of greater than 2.5 meq/g, more preferably greater than 3.5 meq/g, more preferably greater than 4.0 meq/g, more preferably between 4.3 and 4.8 meq/g, even more preferably between 4.4 and 4.7 meq/g, and most preferably approximately 4.5 meq/g. ZS-9 crystals having a potassium exchange capacity in the range of 3.7-3.9 were produced in accordance with Example 13 below. In an embodiment of the invention, the improved ZS-9 crystal compositions (i.e., compositions where the predominant crystalline form is ZS-9) had a potassium exchange capacity of greater than 2.5 meq/g, more preferably between 2.7 and 3.7 meq/g, more preferably between 3.05 and 3.35 meq/g. ZS-9 crystals with a potassium exchange capacity of 3.1 meq/g have been manufactured on a commercial scale and have achieved desirable clinical outcomes. It is expected that ZS-9 crystals with a potassium exchange capacity of 3.2 meq/g will also achieve desirable clinical outcomes and offer improved dosing forms. The targets of 3.1 and 3.2 meq/g may be achieved with a tolerance of ±15%, more preferably ±10%, and most preferably ±5%. Higher capacity forms of ZS-9 are desirable although are more difficult to produce on a commercial scale. Such higher capacity forms of ZS-9 have elevated exchange capacities of greater than 3.5 meq/g, more preferably greater than 4.0 meq/g, more preferably between 4.3 and 4.8 meq/g, even more preferably between 4.4 and 4.7 meq/g, and most preferably approximately 4.5 meq/g. ZS-9 crystals having a potassium exchange capacity in the range of between 3.7 and 3.9 meq/g.

The compositions of the present invention may be used in the treatment of kidney disease (e.g., chronic or acute) or symptoms of kidney diseases, such as hyperkalemia (e.g., chronic or acute) comprising administering the composition to a patient in need thereof. The administered dose may vary, depending on whether the treatment is for chronic or acute hyperkalemia. The dose for treating acute hyperkalemia is higher than that for the treatment of chronic hyperkalemia. For the treatment of acute hyperkalemia, the dose preferably ranges from approximately 0.7 to 1,500 mg/Kg/day, more preferably from approximately 500 to 1,000 mg/Kg/day, and most preferably approximately 700 mg/Kg/day. A typical daily dose for treatment of acute hyperkalemia, depending on the potassium exchange capacity, in a human patient will range from approximately 50 mg to 60 g per day, more preferably from approximately 1 mg to 30 g per day, more preferably 3 to 9 g per day, and most preferably approximately 3 g per day. For the treatment of chronic hyperkalemia, the dose preferably ranges from 0.25 to 100 mg/Kg/day, more preferably from 10 to 70 mg/Kg/day, and most preferably approximately 50 mg/Kg/day. A typical daily dose for treatment of chronic hyperkalemia in a human patient will range from approximately 0.020 to 10 g per day, more preferably from 0.1 to 1 g per day, and most preferably approximately 0.5 g per day.

For higher KEC compositions, the dosages will typically be lower due to the increased effectiveness of the compositions for lowering potassium levels in a patient. For the treatment of acute hyperkalemia, the dose preferably ranges from approximately 0.7 to 800 mg/Kg/day, more preferably from approximately 280 to 500 mg/Kg/day, and most preferably approximately 390 mg/Kg/day. A typical daily dose for treatment of acute hyperkalemia, depending on the potassium exchange capacity, in a human patient will range from approximately 50 mg to 33 g per day, more preferably from approximately 1 mg to 30 g per day, more preferably 3 to 9 g per day, and most preferably approximately 3 g per day. For the treatment of chronic hyperkalemia, the dose preferably ranges from 0.25 to 55 mg/Kg/day, more preferably from 5 to 40 mg/Kg/day, and most preferably approximately 30 mg/Kg/day. A typical daily dose for treatment of chronic hyperkalemia in a human patient will range from approximately 0.020 to 5 g per day, more preferably from 0.05 to 0.7 g per day, and most preferably approximately 0.5 g per day.

Compositions of the invention may be prepared by subjecting a ZS composition as described above to screening or a combination of screening and ion exchange processes as further described herein. Further, the compositions may be prepared using the processes disclosed in the '080 application discussed above.

In another embodiment, the present invention includes the use of pre-existing microporous ZS compositions such as those disclosed in the '080 and '117 applications in the treatment hyperkalemic in hypercalcemic patients. The present inventors have found that ZS compositions lacking added calcium can serve to withdraw excess calcium from patients which makes these compositions useful in the treatment of hyperkalemia in hypercalcemic patents as well as for the treatment of hypercalcemia.

BRIEF DESCRIPTION OF THE DRAWINGS

FIG. 2 shows particle size distribution of ZS-9 lot 5332-04310-A in accordance with Example 8.

FIG. 3 shows particle size distribution of ZS-9 lot 5332-15410-A in accordance with Example 8.

FIG. 4 shows particle size distribution of ZS-9 preclinical lot in accordance with Example 8.

FIG. 5 shows particle size distribution of lot 5332-04310A w/o screening in accordance with Example 9.

FIG. 6 shows particle size distribution of lot 5332-04310A 635 mesh in accordance with Example 9.

FIG. 7 shows particle size distribution of lot 5332-04310A 450 mesh in accordance with Example 9.

FIG. 8 shows particle size distribution of lot 5332-04310A 325 mesh in accordance with Example 9.

FIG. 9 shows particle size distribution of lot 5332-04310A 230 mesh in accordance with Example 9.

FIG. 10: XRD plot for ZS-9 prepared in accordance with Example 12.

FIG. 11: FTIR plot for ZS-9 prepared in accordance with Example 12.

FIG. 12: XRD plot for ZS-9 prepared in accordance with Example 13.

FIG. 13: FTIR plot for ZS-9 prepared in accordance with Example 13.

FIG. 14: Example of the Blank Solution Chromatogram

FIG. 15: Example of the Assay Standard Solution Chromatogram.

FIG. 16: Exemplary Sample Chromatogram.

FIG. 17: Reaction vessel with standard agitator arrangement.

FIG. 18: Reaction vessel with baffles for production of enhanced ZS-9

FIG. 19: Detail of baffle design for 200-L reaction vessel for production of enhanced ZS-9

DETAILED DESCRIPTION OF THE INVENTION

Figure 1:
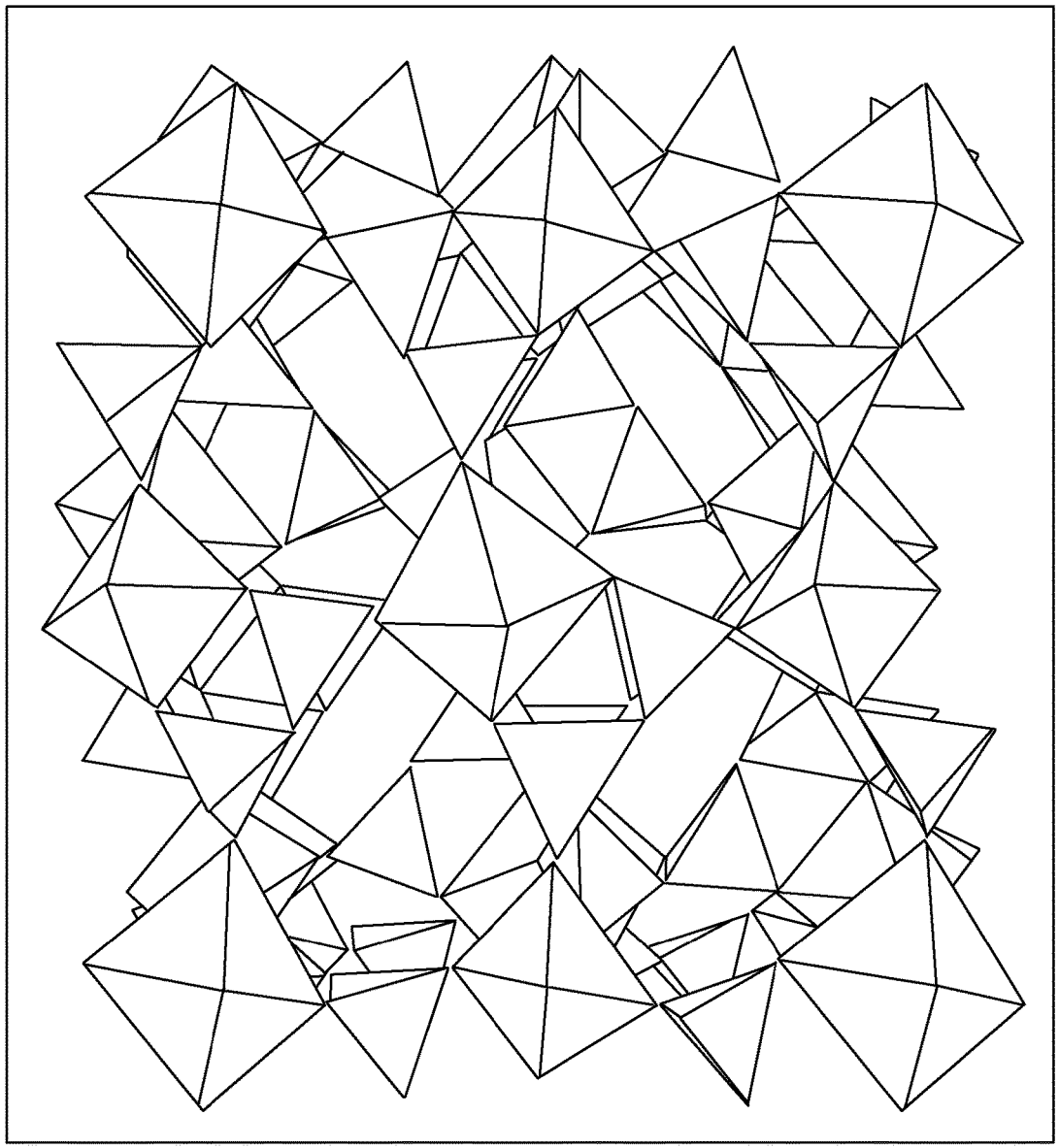
FIG. 1 is a polyhedral drawing showing the structure of microporous ZS $Na_{2.19}ZrSi_{3.01}O_{9.11} \cdot 2.71H_2O$ (MW 420.71)

The inventors have discovered novel ZS molecular sieve absorbers that address problems of adverse effects in the therapeutic use of molecular sieve absorbers, e.g., for the treatment of hyperkalemia. ZS has a microporous framework structure composed of $ZrO_2$ octahedral units and $SiO_2$ tetrahedral units. FIG. 1 is a polyhedral drawing showing the structure of microporous ZS $Na_{2.19}ZrSi_{3.01}O_{9.11} \cdot 2.71H_2O$ (MW 420.71) The dark polygons depict the octahedral zirconium oxide units while the light polygons depict the tetrahedral silicon dioxide units. Cations are not depicted in FIG. 1.

The microporous exchanger of the invention has a large capacity and strong affinity, i.e., selectivity, for potassium or ammonium. Eleven types of ZS are available, ZS-1 through ZS-11, each having various affinities to ions have been developed. See e.g., U.S. Pat. No. 5,891,417. ZS-9 is a particularly effective ZS absorber for absorbing potassium and ammonium. These ZSs have the empirical formula:

$$A_p M_x Zr_{1-x} Si_n Ge_y O_m \quad (I)$$

where A is an exchangeable cation selected from potassium ion, sodium ion, rubidium ion, cesium ion, calcium ion, magnesium ion, hydronium ion or mixtures thereof, M is at least one framework metal selected from the group consisting of hafnium (4+), tin (4+), niobium (5+), titanium (4+), cerium (4+), germanium (4+), praseodymium (4+), and terbium (4+), "p" has a value from about 1 to about 20, "x" has a value from 0 to less than 1, "n" has a value from about 0 to about 12, "y" has a value from 0 to about 12, "m" has a value from about 3 to about 36 and $1 \leq n+y \leq 12$. The germanium can substitute for the silicon, zirconium or combinations thereof. It is preferred that x and y are zero or both approaching zero, as germanium and other metals are often present in trace quantities. Since the compositions are essentially insoluble in bodily fluids (at neutral or basic pH), they can be orally ingested in order to remove toxins in the gastrointestinal system. The inventors of the present invention have noted that ZS-8 has an increased solubility as compared to other forms of ZS (i.e., ZS-1-ZS-7, and ZSi-9-ZS-11). The presence of soluble forms of ZS including ZS-8 are undesirable since soluble forms of ZS may contribute to elevated levels of zirconium and/or silicates in the urine. Amorphous forms of ZS may also be substantially soluble. Therefore, it is desirable to reduce the proportion of amorphous material to the extent practicable.

The zirconium metallates are prepared by a hydrothermal crystallization of a reaction mixture prepared by combining a reactive source of zirconium, silicon and/or germanium, optionally one or more M metal, at least one alkali metal and water. The alkali metal acts as a templating agent. Any zirconium compound, which can be hydrolyzed to zirconium oxide or zirconium hydroxide, can be used. Specific examples of these compounds include zirconium alkoxide, e.g., zirconium n-propoxide, zirconium hydroxide, zirconium acetate, zirconium oxychloride, zirconium chloride, zirconium phosphate and zirconium oxynitrate. The sources of silica include colloidal silica, fumed silica and sodium silicate. The sources of germanium include germanium oxide, germanium alkoxides and germanium tetrachloride. Alkali sources include potassium hydroxide, sodium hydroxide, rubidium hydroxide, cesium hydroxide, sodium carbonate, potassium carbonate, rubidium carbonate, cesium carbonate, sodium halide, potassium halide, rubidium halide, cesium halide, sodium ethylenediamine tetraacetic acid (EDTA), potassium EDTA, rubidium EDTA, and cesium EDTA. The M metals sources include the M metal oxides, alkoxides, halide salts, acetate salts, nitrate salts and sulfate salts. Specific examples of the M metal sources include, but are not limited to titanium alkoxides, titanium tetrachloride, titanium trichloride, titanium dioxide, tin tetrachloride, tin isopropoxide, niobium isopropoxide, hydrous niobium oxide, hafnium isopropoxide, hafnium chloride, hafnium oxychloride, cerium chloride, cerium oxide and cerium sulfate.

Generally, the hydrothermal process used to prepare the zirconium metallate or titanium metallate ion exchange compositions of this invention involves forming a reaction mixture which in terms of molar ratios of the oxides is expressed by the formulae:

$$aA_2O:bMO_{q/2}:1-bZrO_2:cSiO_2:dGeO_2:eH_2O$$

where "a" has a value from about 0.25 to about 40, "b" has a value from about 0 to about 1, "q" is the valence of M, "c" has a value from about 0.5 to about 30, "d" has a value from about 0 to about 30 and "e" has a value of 10 to about 3000. The reaction mixture is prepared by mixing the desired sources of zirconium, silicon and optionally germanium, alkali metal and optional M metal in any order to give the desired mixture. It is also necessary that the mixture have a basic pH and preferably a pH of at least 8. The basicity of the mixture is controlled by adding excess alkali hydroxide and/or basic compounds of the other constituents of the mixture. Having formed the reaction mixture, it is next reacted at a temperature of about 100° C. to about 250° C. for a period of about 1 to about 30 days in a sealed reaction vessel under autogenous pressure. After the allotted time, the mixture is filtered to isolate the solid product which is washed with deionized water, acid or dilute acid and dried. Numerous drying techniques can be utilized including vacuum drying, tray drying, fluidized bed drying. For example, the filtered material may be oven dried in air under vacuum.

To allow for ready reference, the different structure types of the ZS molecular sieves and zirconium germanate molecular sieves have been given arbitrary designations of ZS-1 where the "1" represents a framework of structure type "1". That is, one or more ZS and/or zirconium germanate molecular sieves with different empirical formulas can have the same structure type.

The X-ray patterns presented in the following examples were obtained using standard X-ray powder diffraction techniques and reported in U.S. Pat. No. 5,891,417. The radiation source was a high-intensity X-ray tube operated at 45 Kv and 35 ma. The diffraction pattern from the copper K-alpha radiation was obtained by appropriate computer based techniques. Flat compressed powder samples were continuously scanned at 2° (2θ) per minute. Interplanar spacings (d) in Angstrom units were obtained from the position of the diffraction peaks expressed as 2 θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art, the determination of the parameter 2θ is subject to both human and mechanical error, which in combination can impose an uncertainty of about ±0.4 on each reported value of 2θ. This uncertainty is, of course, also manifested in the reported values of the d-spacings, which are calculated from the θ values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m and w which represent very strong, strong, medium, and weak, respectively. In terms of $100 \times I/I_o$, the above designations are defined as w=0-15; m=15-60; s=60-80 and vs=80-100.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The crystalline compositions of the instant invention may be characterized by their X-ray powder diffraction patterns and such may have one of the X-ray patterns containing the d-spacings and intensities set forth in the following Tables. The x-ray pattern for ZS-1, ZS-2, ZS-6, ZS-7, ZS-8, and ZS-11 as reported in U.S. Pat. No. 5,891,417, is as follows:

TABLE 1

ZS X-Ray powder diffraction patterns

| d(Å) | I |
|---|---|
| ZS-1 | |
| 7.7-8.6 | m |
| 6.3-7.0 | m |
| 5.5-6.3 | s |
| 4.7-5.5 | m |
| 3.2-4.0 | m |
| 2.6-3.4 | vs |
| ZS-2 | |
| 5.8-6.6 | m |
| 4.2-5.0 | w |
| 3.9-4.6 | m |
| 2.9-3.7 | m |
| 2.5-3.3 | vs |
| 2.3-3.0 | s |
| ZS-6 | |
| 6.1-6.9 | m |
| 4.4-5.1 | m |
| 3.4-4.2 | m |
| 3.3-4.1 | m |
| 2.3-3.1 | vs |
| 2.2-3.0 | w |
| ZS-7 | |
| 6.8-7.6 | vs |
| 5.6-6.4 | m |
| 3.7-4.5 | m |
| 3.6-4.4 | m |
| 2.6-3.4 | s-vs |
| 2.5-3.3 | m |
| 2.4-3.2 | vs |
| ZS-8 | |
| 12.0-13.2 | vs |
| 3.9-4.7 | m |

TABLE 1-continued

ZS X-Ray powder diffraction patterns

| d(Å) | I |
|---|---|
| 2.8-3.6 | m |
| 2.3-3.1 | m |
| 2.2-3.0 | w |
| 2.1-2.9 | w |
| ZS-11 | |
| 6.0-6.8 | w-m |
| 5.5-6.3 | m |
| 5.4-6.2 | vs |
| 5.2-6.0 | m |
| 2.7-3.5 | s |
| 2.5-3.3 | m |

The x-ray diffraction pattern for the high-purity, high KEC ZS-9 as made in accordance with Example 13 herein (XRD shown in FIG. 13), had the following characteristics d-spacing ranges and intensities:

TABLE 2

| ZS-9 | |
|---|---|
| d(Å) | I |
| 5.9-6.7 | m |
| 5.3-6.1 | m-s |
| 2.7-3.5 | vs |
| 2.0-2.8 | w-m |
| 1.6-2.4 | w |

The formation of ZS involves the reaction of sodium silicate and zirconium acetate in the presence of sodium hydroxide and water. The reaction has typically been conducted in small reaction vessels on the order of 1-5 Gallons. The smaller reaction vessels have been used to produce various crystalline forms of ZS including ZS-9. The inventors recognized that the ZS-9 being produced in these smaller reactors had an inadequate or undesirably low cation exchange capacity (CEC).

The inventors have discovered that the use and proper positioning of a baffle-like structure in relation to the agitator within the crystallization vessel produces a ZS-9 crystal product exhibiting crystalline purity (as shown by XRD and FTIR spectra) and an unexpectedly high potassium exchange capacity. In smaller scale reactors (5-gal), cooling coils were positioned within the reactor to provide a baffle-like structure. The cooling coils were not used for heat exchange. Several types of cooling coils are available and the different designs may have some effect on the results presented herein, but the inventors used serpentine-type coils which snake along the inside wall of the reactor vessel.

The inventors found that the crystallization reaction used to produce ZS-9 particularly benefitted from baffles that when they are properly positioned relative to the agitator. The inventors initially produced ZS-9 with significant levels of undesirable ZS-11 impurity. See FIGS. 10-11. This incomplete reaction is believed to have resulted from significant amounts of solids remaining near the bottom of the reaction vessel. These solids near the bottom of the vessel remain even with conventional agitation. When properly positioned, the baffles and agitator improved the reaction conditions by creating forces within the reactor that lift the crystals within the vessel allowing for the necessary heat transfer and agitation to make a high purity form of ZS-9. In one embodiment, the baffles in combination with the agitator may be configured such that it provides sufficient lift throughout the entire volume regardless of the size of the reactor used. For example, if the reactor size is enlarged (e.g., 200 liter reactor) and the reaction volume is increased, the baffles will also be resized to accommodate the new reactor volume. FIGS. 11-12 show XRD and FTIR spectra of high purity ZS-9 crystals. As shown in Table 3 below, these crystals exhibit significantly higher levels of potassium exchange capacity (KEC) than the less pure ZS-9 compositions. In an embodiment of the invention, the ZS-9 crystals had a potassium exchange capacity of between 2.7 and 3.7 meq/g, more preferably between 3.05 and 3.35 meq/g. ZS-9 crystals with a potassium exchange capacity of 3.1 meq/g have been manufactured on a commercial scale and have achieved desirable clinical outcomes. It is expected that ZS-9 crystals with a potassium exchange capacity of 3.2 meq/g will also achieve desirable clinical outcomes and offer improved dosing forms. The targets of 3.1 and 3.2 meq/g may be achieved with a tolerance of ±15%, more preferably ±10%, and most preferably ±5%. Higher capacity forms of ZS-9 are desirable although are more difficult to produce on a commercial scale. Such higher capacity forms of ZS-9 have elevated exchange capacities of greater than 3.5 meq/g, preferably greater than 4.0 meq/g, more preferably between 4.3 and 4.8 meq/g, even more preferably between 4.4 and 4.7 meq/g, and most preferably approximately 4.5 meq/g. ZS-9 crystals having a potassium exchange capacity in the range of between 3.7 and 3.9 meq/g were produced in accordance with Example 13 below.

Another unexpected benefit that came from using the reactor having a standard agitator in combination with baffles is that the high crystalline purity, high potassium exchange capacity ZS-9 crystals could be produced without utilizing any seed crystals. Prior attempts at making homogenous crystals having high crystalline purity of a single crystalline form have utilized seed crystals. The ability to eliminate the use of seed crystals was therefore an unexpected improvement relative to prior art processes.

As stated the microporous compositions of this invention have a framework structure of octahedral $ZrO_3$ units, at least one of tetrahedral $SiO_2$ units and tetrahedral $GeO_2$ units, and optionally octahedral $MO_3$ units. This framework results in a microporous structure having an intracrystalline pore system with uniform pore diameters, i.e., the pore sizes are crystallographically regular. The diameter of the pores can vary considerably from about 3 angstroms and larger.

As synthesized, the microporous compositions of this invention will contain some of the alkali metal templating agent in the pores. These metals are described as exchangeable cations, meaning that they can be exchanged with other (secondary) A' cations. Generally, the A exchangeable cations can be exchanged with A' cations selected from other alkali metal cations ($K^+$, $Na^+$, $Rb^+$, $Cs^+$), alkaline earth cations ($Mg^{2+}$, $Ca^{2+}$, $Sr^{2+}$, $Ba^{2+}$), hydronium ion or mixtures thereof. It is understood that the A' cation is different from the A cation. The methods used to exchange one cation for another are well known in the art and involve contacting the microporous compositions with a solution containing the desired cation (usually at molar excess) at exchange conditions. Typically, exchange conditions include a temperature of about 25° C. to about 100° C. and a time of about 20 minutes to about 2 hours. The use of water to exchange ions to replace sodium ions with hydronium ions may require more time, on the order of eight to ten hours. The particular cation (or mixture thereof) which is present in the final product will depend on the particular use and the specific composition being used. One particular composition is an ion exchanger where the A' cation is a mixture of $Na^+$, $Ca^{+2}$, $Mg^{2+}$, a mixture of both $Ca^{+2}$ and $Mg^{2+}$, and $H^+$ ions.

When ZS-9 is formed according to these processes, it can be recovered in the Na-ZS-9 form. The sodium content of Na-ZS-9 is approximately 12 to 13% by weight when the manufacturing process is carried out at pH greater than 9. The Na-ZS-9 is unstable in concentrations of hydrochloric acid (HCl) exceeding 0.2 M at room temperature, and will undergo structural collapse after overnight exposure. While ZS-9 is slightly stable in 0.2 M HCl at room temperature, at 37° C. the material rapidly loses crystallinity. At room temperature, Na-ZS-9 is stable in solutions of 0.1M HCl and/or a pH of between approximately 6 to 7. Under these conditions, the Na level is decreased from 13% to 2% upon overnight treatment.

The conversion of Na-ZS-9 to H-ZS-9 may be accomplished through a combination of water washing and ion exchange processes, i.e., ion exchange using a dilute strong acid, e.g., 0.1 M HCl or by washing with water. Washing with water will decrease the pH and protonate a significant fraction of the ZS, thereby lowering the weight fraction of Na in the ZS. It may be desirable to perform an initial ion exchange in strong acid using higher concentrations, so long as the protonation of the ZS will effectively keep the pH from dropping to levels at which the ZS decomposes. Additional ion exchange may be accomplished with washing in water or dilute acids to further reduce the level of sodium in the ZS. The ZS made in accordance with the present invention exhibits a sodium content of below 12% by weight. Preferably, the sodium contents is below 9% by weight, more preferably the sodium content is below 6% by weight, more preferably the sodium content is below 3% by weight, more preferably the sodium content is in a range of between 0.05 to 3% by weight, and most preferably 0.01% or less by weight or as low as possible. When protonated (i.e., low sodium) ZS is prepared in accordance with these techniques, the potassium exchange capacity is lowered relative to the un-protonated crystals. The ZS prepared in this way has a potassium exchange capacity of greater than 2.8. In a preferred aspect, the potassium exchange capacity is within the range of 2.8 to 3.5 meq/g, more preferably within the range of 3.05 and 3.35 meq/g, and most preferably about 3.2 meq/g. A potassium exchange capacity target of about 3.2 meq/g includes minor fluctuations in measured potassium exchange capacity that are expected between different batches of ZS crystals.

It has been found that when ZS crystals produced under optimal crystalline conditions are protonated, the protonation can result in a loss in cation exchange capacity. The inventors have discovered during scale up of the manufacturing process for ZS-9 that where crystallization conditions are less than optimal, the protonation of the produced ZS crystals results in an increased cation exchange capacity relative to the unprotonated form. The suboptimal crystallization conditions result for challenges of maintaining thorough agitation in a larger reaction vessel. For example, when increasing the size of the reaction vessel from a 50 gallons to 125 gallons, ZS-9 crystals with a crystalline impurities were produced. However, assessment of the KEC values for the protonated H-ZS-9 crystals utilizing this new method provided for greater than expected KEC's of greater than 3.1 meq/g, more preferably in the range of 3.2 to 3.5 meq/g.

The ion exchanger in the sodium form, e.g., Na-ZS-9, is effective at removing excess potassium ions from a patient's gastrointestinal tract in the treatment of hyperkalemia. When the sodium form is administered to a patient, hydronium ions replace sodium ions on the exchanger leading to an unwanted rise in pH in the patient's stomach and gastrointestinal tract. Through in vitro tests it takes approximately twenty minutes in acid to stabilize sodium ion exchanger.

The hydronium form typically has equivalent efficacy as the sodium form for removing potassium ions in vivo while avoiding some of the disadvantages of the sodium form related to pH changes in the patient's body. For example, the hydrogenated form has the advantage of avoiding excessive release of sodium in the body upon administration. This can mitigate edema resulting from excessive sodium levels, particularly when used to treat acute conditions. Further, patient who are administered the hydronium form to treat chronic conditions will benefit from the lower sodium levels, particularly patients at risk for congestive heart failure. Further, it is believed that the hydronium form will have the effect of avoiding an undesirable increase of pH in the patient's urine.

The present inventors have found that ZS compositions lacking added calcium can serve to withdraw excess calcium from patients which makes these compositions useful in the treatment of hyperkalemia in hypercalcemic patents as well as for the treatment of hypercalcemia. The calcium content of compositions prepared according to the process above is typically very low, i.e., below 1 ppm. The present inventors have found that treatment of hyperkalemia with these compositions is also associated with removal of significant quantities of calcium from the patient's body. Therefore, these compositions are particularly useful for the treatment of hypercalcemic patients or hypercalcemic patients suffering from hyperkalemic.

The compositions of the present invention are prepared by pre-loading the above-described ZS compositions with calcium ions. The pre-loading of the compositions with calcium results in a composition that will not absorb calcium when administered to patients.

The pre-loading of ZS with calcium (and/or magnesium) is accomplished by contacting the ZS with a dilute solution of either calcium or magnesium ions, preferably having a calcium or magnesium concentration range of about 10-100 ppm. The pre-loading step can be accomplished simultaneously with the step of exchanging hydronium ions with sodium ions as discussed above. Alternatively, the pre-loading step can be accomplished by contacting ZS crystals at any stage of their manufacture with a calcium or magnesium containing solution. Preferably, the ZS compositions comprise calcium or magnesium levels ranging from 1 to 100 ppm, preferably from 1 to 30 ppm, and more preferably between 5 and 25 ppm.

The composition of the present invention may also be prepared by pre-loading the ZS with a dilute solution of magnesium ion or a mixture of both calcium and magnesium according to the method described above. Preferably, the magnesium concentration is in the range of about 10-100 ppm, preferably 1-30 ppm, and more preferably 5-25 ppm. Pre-loaded ZS compositions with a mixture of both calcium and magnesium are at a ratio of calcium to magnesium in a range of 1:10 to 10:1, preferably 1:5 to 5:1, or more preferably 1:2 to 2:1, wherein the final concentration of both calcium to magnesium does not exceed the range of 10-100 ppm, preferably 1-30 ppm, more preferably 5-125 ppm. The pre-loaded ZS, regardless of the divalent cation used, does not affect the potassium exchange concentration of the composition. The skilled practitioner will be capable of determining the appropriate concentrations of the divalent cation such that the potassium exchange rates of the ZSs are not effected.

The pre-loading of ZS does not result in a reduction in potassium absorption capacity and therefore does not detract from the use of these compositions in the treatment of hyperkalemia. It is believed that due to their size, divalent cations, such as calcium or magnesium ions, do not fully penetrate the pores of the ZS. Rather, the loaded divalent cations remain only on the surface of the ZS. The added divalent cations result in a composition that does not absorb calcium from the patient's body and therefore is preferred for clinical use in the treatment of hyperkalemia.

In another embodiment, protonated ZS may be linked to hydroxyl-loaded anion exchanger such as zirconium oxide (OH—ZO), which help in the removal of sodium, potassium, ammonium, hydrogen and phosphate. Without being bound to a theory, the hydrogen released from the protonated ZS and hydroxide released from OH—ZO combine to form water, thus diminishing the concentration of "counter-ions" which diminish binding of other ions. The binding capacity of the cation and anion exchangers should be increased by administering them together. ZS of this form are useful for the treatment of many different types of diseases. In one embodiment, the compositions are used to remove sodium, potassium, ammonium, hydrogen and phosphate from the gut and from the patient with kidney failure.

The ZS-9 crystals have a broad particle size distribution. It has been theorized that small particles, less than 3 microns in diameter, could potentially be absorbed into a patient's bloodstream resulting in undesirable effects such as the accumulation of particles in the urinary tract of the patient, and particularly in the patent's kidneys. The commercially available ZSs are manufactured in a way that some of the particles below 1 micron are filtered out. However, it has been found that small particles are retained in the filter cake and that elimination of particles having a diameter less than 3 microns requires the use of additional screening techniques.

The inventors have found that screening can be used to remove particles having a diameter below 3 microns and that removal of such particles is beneficial for therapeutic products containing the ZS compositions of the invention. Many techniques for particle screening can be used to accomplish the objectives of the invention, including hand screening, air jet screening, sifting or filtering, floating or any other known means of particle classification. ZS compositions that have been subject to screening techniques exhibit a desired particle size distribution that avoids potential complications involving the therapeutic use of ZS. In general, the size distribution of particles is not critical, so long as excessively small particles are removed. The ZS compositions of the invention exhibit a median particle size greater than 3 microns, and less than 7% of the particles in the composition have a diameter less than 3 microns. Preferably, less than 5% of the particles in the composition have a diameter less than 3 microns, more preferably less than 4% of the particles in the composition have a diameter less than 3 microns, more preferably less than 3% of the particles in the composition have a diameter of less than 3 microns, more preferably less than 2% of the particles in the composition have a diameter of less than 3 microns, more preferably less than 1% of the particles in the composition have a diameter of less than 3 microns, more preferably less than 0.5% of the particles in the composition have a diameter of less than 3 microns. Most preferably, none of the particles or only trace amounts have a diameter of less than 3 microns. The median particle size is preferably greater than 3 microns and particles reaching a sizes on the order of 1,000 microns are possible for certain applications. Preferably, the median particle size ranges from 5 to 1000 microns, more preferably 10 to 600 microns, more preferably from 15 to 200 microns, and most preferably from 20 to 100 microns.

The particle screening can be conducted before, during, or after an ion exchange process such as described above whereby the sodium content of the ZS material is lowered below 12%. The lowering of sodium content to below 3% can occur over several steps in conjunction with screening or can occur entirely before or after the screening step. Particles having a sodium content below 3% may be effective with or without screening of particles sizes as described herein.

In addition to screening or sieving, the desired particle size distribution may be achieved using a granulation or other agglomeration technique for producing appropriately sized particles.

In another embodiment, the ZS compositions may further comprise atoms or molecules attached onto their surfaces to produced grafted crystals. The grafted atoms or molecules are attached to the surface of the ZS, preferably through stable covalent bonds. In one embodiment, an organosilicate moiety is grafted onto the surface of the ZS composition through reacting active groups such as silanols ($\equiv$Si—O—H) on the surface of crystals. This may be accomplished, for example by using aprotic solvents. In another embodiment, an alkoxysilane may be grafted and would require the use of a corresponding alcohol to perform the reaction. Identifying free silanol groups on the surface can done through, for example by, Infrared spectroscopy. In another embodiment, if the material to graft lacks of the active groups on their surface, acid washes can be used to promote their formation. Following successful grafting, the ZS compositions may further comprise tagging the composition with radioactive isotopes, such as but not limited to C or Si. In an alternative embodiment, the ZS compositions may also comprise non-exchangeable atoms, such as isotopes of Zr, Si, or O, which may be useful in mass-balance studies.

It is also within the scope of the invention that these microporous ion exchange compositions can be used in powder form or can be formed into various shapes by means well known in the art. Examples of these various shapes include pills, extrudates, spheres, pellets and irregularly shaped particles. It is also envisioned that the various forms can be packaged in a variety of known containers. These might include capsules, plastic bags, pouches, packets, sachets, dose packs, vials, bottles, or any other carrying device that is generally known to one of skill in the art.

It is also envisioned that the various forms can be packaged in a variety of known containers. These might include capsules, plastic bags, pouches, packets, sachets, dose packs, vials, bottles, or any other carrying device that is generally known to one of skill in the art.

The microporous ion exchange crystals of this invention may be combined with other materials to produce a composition exhibiting a desired effect. The ZS compositions may be combined with foods, medicaments, devices, and compositions that are used to treat a variety of diseases. For example, the ZS compositions of the present invention may be combined with toxin reducing compounds, such as charcoal, to expedite toxin and poison removal. In another embodiment, the ZS crystals may exist as a combination of two or more forms of ZS of ZS-1 to ZS-11. In one embodiment, the combination of ZS may comprise ZS-9 and ZS-11, more preferably ZS-9 and ZS-7, even more preferably ZS-9, ZS-11, and ZS-7. In another embodiment of the present invention, the ZS composition may comprise a blend or mixture of ZS-9, wherein ZS-9 is present at greater than at least 40%, more preferably greater than at least 60%, even more preferably greater than or equal 70%, where the remainder may comprise mixtures of other forms of ZS crystals (i.e., ZS-1 to ZS-11) or other amorphous forms. In another embodiment, the blend of ZS-9 may comprise greater than about between 50% to 75% ZS-9 crystals and greater than about 25% to about 50% ZS-7 crystals with the remainder being other forms of ZS crystals, wherein the remainder of the ZS crystals does not include ZS-8 crystals.

As stated, these compositions have particular utility in adsorbing various toxins from fluids selected from bodily fluids, dialysate solutions, and mixtures thereof. As used herein, bodily fluids will include but not be limited to blood and gastrointestinal fluids. Also by bodily is meant any mammalian body including but not limited to humans, cows, pigs, sheep, monkeys, gorillas, horses, dogs, etc. The instant process is particularly suited for removing toxins from a human body.

The zirconium metallates can also be formed into pills or other shapes which can be ingested orally and pickup toxins in the gastrointestinal fluid as the ion exchanger transits through the intestines and is finally excreted. In one embodiment, the ZS compositions may be made into wafer, a pill, a powder, a medical food, a suspended powder, or a layered structure comprising two or more ZS. In order to protect the ion exchangers from the high acid content in the stomach, the shaped articles may be coated with various coatings which will not dissolve in the stomach, but dissolve in the intestines. In one embodiment, the ZS may be shaped into a form that is subsequently coated with an enteric coating or embedded within a site specific tablet, or capsule for site specific delivery.

As has also been stated, although the instant compositions are synthesized with a variety of exchangeable cations ("A"), it is preferred to exchange the cation with secondary cations (A') which are more compatible with blood or do not adversely affect the blood. For this reason, preferred cations are sodium, calcium, hydronium and magnesium. Preferred compositions are those containing sodium and calcium, sodium, calcium and magnesium sodium, and hydronium ions, sodium, magnesium, and hydronium ions, or sodium, calcium and hydronium ions, sodium, magnesium, and/or magnesium, or sodium calcium and/or magnesium, and hydronium ions. The relative amount of sodium and calcium and/or magnesium can vary considerably and depends on the microporous composition and the concentration of these ions in the blood. As discussed above, when sodium is the exchangeable cation, it is desirable to replace the sodium ions with hydronium ions thereby reducing the sodium content of the composition.

ZS crystals as described in related U.S. application Ser. No. 13/371,080, which is incorporated by reference in its entirety, have increased cation exchange capacities or potassium exchange capacity. These increased capacity crystals may also be used in accordance with the present invention. The dosage utilized in formulating the pharmaceutical composition in accordance to the present invention will be adjusted according to the cation exchange capacities determined by those of skill in the art. Accordingly, the amount of crystals utilized in the formulation will vary based on this determination. Due to its higher cation exchange capacity, less dosage may be required to achieve the same effect.

The compositions of the present invention may be used in the treatment of diseases or conditions relating to elevated serum potassium levels. These disease may include for example chronic or acute kidney disease, chronic, acute or sub-acute hyperkalemia. To those patients suffering from diseases or conditions with elevated serum potassium levels, the product of the present invention is administered at specific potassium reducing dosages. The administered dose ranges from approximately 1.25-15 grams (~18-215 mg/Kg/day, preferably from approximately 500 to 1,000 mg/Kg/day, and most preferably approximately 10 grams (~140 mg/Kg/day) three times a day. In another embodiment, the total administered dose of the composition may range from approximately 15-45 gram (~215-640 mg/Kg/day), preferably 24-36 grams (~350-520 mg/Kg/day), and more preferably 30 grams (~400 mg/Kg/day).). When administered to a subject, the composition of the present invention is capable of decreasing the serum potassium levels to near normal levels of approximately 3.5-5 mmol/L. The molecular sieves of the present product are capable of specifically removing potassium without affecting other electrolytes, (i.e., no hypomagnesemia or no hypocalcemia). The use of the present product or composition is accomplished without the aid of laxatives or other resins for the removal of excess serum potassium.

For higher KEC compositions, the dosages will typically be lower due to the increased effectiveness of the compositions for lowering potassium levels in a patient. For the treatment of acute hyperkalemia, the dose preferably ranges from approximately 0.7 to 800 mg/Kg/day, more preferably from approximately 280 to 500 mg/Kg/day, and most preferably approximately 390 mg/Kg/day. A typical daily dose for treatment of acute hyperkalemia, depending on the potassium exchange capacity, in a human patient will range from approximately 50 mg to 33 g per day, more preferably from approximately 1 mg to 30 g per day, more preferably 3 to 9 g per day, and most preferably approximately 3 g per day. For the treatment of chronic hyperkalemia, the dose preferably ranges from 0.25 to 55 mg/Kg/day, more preferably from 5 to 40 mg/Kg/day, and most preferably approximately 30 mg/Kg/day. A typical daily dose for treatment of chronic hyperkalemia in a human patient will range from approximately 0.020 to 5 g per day, more preferably from 0.05 to 0.7 g per day, and most preferably approximately 0.5 g per day.

Acute hyperkalemia requires an immediate reduction of serum potassium levels to normal or near normal levels. Molecular sieves of the present invention which have a KEC in the range of approximately 1.3-2.5 meq/g would be capable of lowering the elevated levels of potassium to within normal range in a period of about 1-8 hours after administration. In one embodiment, the product of the present invention is capable of lowering the elevated levels in about at least 1, 2, 4, 6, 8, 10 hours after administration. The dose required to reduce the elevated potassium levels may be in the range of about 5-15 grams, preferably 8-12 grams, more preferably 10 grams. Molecular sieves having a higher KEC in the range of approximately 2.5-4.7 meq/g would be more efficient in absorbing potassium. As a result, the dose required to reduce the elevated potassium levels may be in the range of about 1.25-6 grams. The schedule of dose administration may be at least once daily, more preferably three times a day.

The treatment of chronic and sub-acute hyperkalemia will require maintenance dosing to keep potassium levels near or within normal serum potassium levels. As such, the administration of the product of the present invention will be lower than that prescribed to patients suffering from acute hyperkalemia. In one embodiment, compositions comprising molecular sieves having KEC in the range of approximately 2.5-4.7 meq/g will be scheduled for a dose in the range of approximately 1-5 grams, preferably 1.25-5 grams, preferably 2.5-5 grams, preferably 2-4 grams, more preferably 2.5 grams. Compositions comprising molecular sieves having a KEC in the range of approximately 2.5-4.7 meq/g will receive less and will be scheduled for a dose in the range of approximately 0.4-2.5 grams, preferably 0.8-1.6 grams, preferably 1.25-5 grams, preferably 2.5-5 grams, more preferably 1.25 grams. Compliance in this subset of patients is a major factor in maintaining normal potassium levels. As such, dosing schedule will therefore be an important consideration. In one embodiment, the dose will be given to patients at least three times a day, more preferably once a day.

The composition or product of the present invention may be formulated in a manner that is convenient for administration. For example, the composition of the present invention may be formulated as a tablet, capsule, powder, granule, crystal, packet, or any other dose form that is generally known to one of skill in the art. The various forms can be formulated as individual dosages comprising between 5-15 grams, preferably 8-12 grams, or more preferably 10 grams for multiple administrations per day, week or month; or they may be formulated as a single dosage comprising between 15-45 grams, preferably 24-36 grams, or more preferably 30 grams. In an alternative embodiment, the individual dosage form can be at least greater than 1, 2, 3, 4, 5, 6, 7, 8, 9, 10, 20, 30, or 40 grams. If the dosage form is tablet, it may be formulated as a granule, granule-like, or as an extended release form. Capsules may be formulated for administration three times a day, as a sprinkle, an extended release sprinkle, or a dose pack. Powders may be formulated for reconstitution, contained in plastic bags or packets. Those of skill in the art will recognize that the above description of dosage forms is not limiting and that other dosage forms for solids may be used to administer the product or composition of the present invention.

Surprisingly, the administration of the composition of the present invention at the specifically described dosing of approximately 10 grams (~140 mg/Kg/day) three times a day (i.e., 30 grams (~400 mg/Kg/day) total) is capable of reducing potassium levels in the serum for an extended duration of time. The inventors have found that when the product or composition of the present invention is administered at a dosage of approximately 10 grams three times a day, the effects of lowering serum potassium levels to within normal levels is sustained for 5 days after 2 days of acute therapy. It was expected, however, that the product of the present invention would be expelled in a relatively quick manner.

The ZS of the present invention may be modified and/or combined with other drugs or treatments if multiple conditions or diseases are present in a subject. For example, in one embodiment a subject may present with both hyperkalemia and chronic kidney disease, in which Na-ZS compositions may be used. In another embodiment, the ZS compositions used to treat chronic kidney disease may further comprise sodium bicarbonate in combination with protonated forms of the ZS. In another embodiment, subjects presenting with hyperkalemia and chronic heart failure may require the use of protonated ZS compositions. In another embodiment, the treatment of hyperkalemia and chronic heart disease will require no more than 10% sodium present in the ZS, more preferably less than 2% sodium.

In other embodiments of the invention, the ZS described herein may be further combined with activated carbon. The activated carbon has the effect of attracting organic molecules circulating within the system of a subject. See, e.g., HSGD Haemosorbents for Medical Device Applications, Nikolaev V. G. Presentation, London. As such, the combination of activated carbon with a ZS will act as a combination product having the ability to remove both excess potassium, and organic molecules. The activated carbon will comprise a multiplicity of adsorption pores of ranging from about 8 angstroms to about 800 angstroms in diameter, preferably at least about 50 angstroms in diameter. The ZS combined with activated carbon of the present invention will be useful in the treatment of many diseases and/or conditions requiring the removal of excess organic materials, such as but not limited to, lipids, proteins, and toxins. For example, the carbon containing ZS compositions of the present invention will be useful in the removal of pyrimidines, methylguanidines, guanidines, o-hydroxyhippuric acid, p-hydroxyhippuric acid, parathormone, purines, phenols, indols, pesticides, carcinogenic heterocyclic amines, conjugates of ascorbic acids, trihalomethanes, dimethylarginine, methylamines, organic chloramines, polyamines, or combinations thereof. The activated carbon combined with ZS will also be useful in adsorbing elevated levels of bile acids, albumin, ammonia, creatinine and bilirubin. To further improve the adsorption of activated carbon with coated ZS, the composition may be further coated with an albumin layer, a lipid layer, a DNA layer, a heparin layer, resulting in additional adsorption efficiencies ranging from about 12% to about 35%.

The activated carbon and ZS compositions will be useful in treating a subject presenting with multiple diseases or conditions, such as hyperkalemia, acute and chronic esogastritis, acute and chronic intestinal catarrhus, hyperacid gastritis, summer diarrhea, catarrhal jaundice, food related toxicoinfections, kidney disease, dysentery, choloera, typhoid, intestinal bacilli-carrier, heartburn, nausea, acute viral hepatitis, chronic active hepatitis and cirrhosis, concomitant hepatitis, mechanical jaundice, hepato-renal failure, hepatic coma, or combinations thereof.

In another embodiment, the ZS compositions described herein may be used in a variety of methods comprising administering to a subject in need thereof a composition described herein to remove excess levels of potassium. In another embodiment of the present invention, the method may include the administration of a combination of the ZS described herein and may further comprise additional compositions to aid in the removal of potassium while simultaneously removing other substances, such as but not limited to toxins, proteins, or ions, from the subject.

In order to more fully illustrate the invention, the following examples are set forth. It is to be understood that the examples are only by way of illustration and are not intended as an undue limitation on the broad scope of the invention as set forth in the appended claims.

EXAMPLE 1

A solution was prepared by mixing 2058 g of colloidal silica (DuPont Corp. identified as Ludox™ AS-40), 2210 g of KOH in 7655 g $H_2O$. After several minutes of vigorous stirring 1471 g of a zirconium acetate solution (22.1 wt. % $ZrO_2$) were added. This mixture was stirred for an additional 3 minutes and the resulting gel was transferred to a stainless steel reactor and hydrothermally reacted for 36 hours at 200° C. The reactor was cooled to room temperature and the mixture was vacuum filtered to isolate solids which were washed with deionized water and dried in air.

The solid reaction product was analyzed and found to contain 21.2 wt. % Si, 21.5 wt. % Zr, K 20.9 wt. % K, loss on ignition (LOI) 12.8 wt. %, which gave a formula of $K_{2.3}ZrSi_{3.2}O_{9.5}*3.7H_2O$. This product was identified as sample A.

EXAMPLE 2

A solution was prepared by mixing 121.5 g of colloidal silica (DuPont Corp. identified as Ludox® AS-40), 83.7 g of NaOH in 1051 g $H_2O$. After several minutes of vigorous stirring 66.9 g zirconium acetate solution (22.1 wt. % $ZrO_2$) was added. This was stirred for an additional 3 minutes and the resulting gel was transferred to a stainless steel reactor and hydrothermally reacted with stirring for 72 hours at 200° C. The reactor was cooled to room temperature and the mixture was vacuum filtered to isolate solids which were washed with deionized water and dried in air.

The solid reaction product was analyzed and found to contain 22.7 wt. % Si, 24.8 wt. % Zr, 12.8 wt. % Na, LOI 13.7 wt. %, which gives a formula $Na_{2.0}ZrSi_{3.0}O_{9.0}*3.5H_2O$. This product was identified as sample B.

EXAMPLE 3

A solution (60.08 g) of colloidal silica (DuPont Corp. identified as Ludox® AS-40) was slowly added over a period of 15 minutes to a stirring solution of 64.52 g of KOH dissolved in 224 g deionized $H_2O$. This was followed by the addition of 45.61 g zirconium acetate (Aldrich 15-16 wt. % Zr, in dilute acetic acid). When this addition was complete, 4.75 g hydrous $Nb_2O_5$ (30 wt. % LOI) was added and stirred for an additional 5 minutes. The resulting gel was transferred to a stirred autoclave reactor and hydrothermally treated for 1 day at 200° C. After this time, the reactor was cooled to room temperature, the mixture was vacuum filtered, the solid washed with deionized water and dried in air.

The solid reaction product was analyzed and found to contain 20.3 wt. % Si, 15.6 wt. % Zr, 20.2 wt. % K, 6.60 wt. % Nb, LOI 9.32 wt. %, which give a formula of $K_{2.14}Zr_{0.71}Nb_{0.29}Si_3O_{9.2}*2.32H_2O$. Scanning Electron (SEM) of a portion of the sample, including EDAX of a crystal, indicated the presence of niobium, zirconium, and silicon framework elements. This product was identified as sample C.

EXAMPLE 4

To a solution prepared by mixing 141.9 g of NaOH pellets in 774.5 g of water, there were added 303.8 g of sodium silicate with stirring. To this mixture there were added dropwise, 179.9 g of zirconium acetate (15% Zr in a 10% acetic acid solution). After thorough blending, the mixture was transferred to a Hastalloy™ reactor and heated to 200° C. under autogenous pressure with stirring for 72 hours. At the end of the reaction time, the mixture was cooled to room temperature, filtered and the solid product was washed with a 0.001 M NaOH solution and then dried at 100° C. for 16 hours. Analysis by x-ray powder diffraction showed that the product was pure ZS-11.

EXAMPLE 5

To a container there was added a solution of 37.6 g NaOH pellets dissolved in 848.5 g water and to this solution there were added 322.8 g of sodium silicate with mixing. To this mixture there were added dropwise 191.2 g of zirconium acetate (15% Zr in 10% acetic acid). After thorough blending, the mixture was transferred to a Hastalloy™ reactor and the reactor was heated to 200° C. under autogenous conditions with stirring for 72 hours. Upon cooling, the product was filtered, washed with 0.001 M NaOH solution and then dried at 100° C. for 16 hours. X-ray powder diffraction analysis showed the product to be ZS-9.

EXAMPLE 6

Approximately 57 g (non-volatile-free basis, lot 0063-58-30) of Na-ZS-9 was suspended in about 25 mL of water. A solution of 0.1N HCl was added gradually, with gentle stirring, and pH monitored with a pH meter. A total of about 178 milliliters of 0.1 N HCl was added with stirring, the mixture filtered then further rinsed with additional 1.2 liters 0.1 N HCl washes. The material was filtered, dried and washed with DI water. The pH of the resulting material was 7.0. The H-ZS-9 powder resulting from this three batch-wise ion exchange with 0.1 N HCl has <12% Na.

As illustrated in this example, batch-wise ion exchange with a dilute strong acid is capable of reducing the sodium content of a NA-ZS-9 composition to within a desired range.

EXAMPLE 7

Approximately 85 gram (non-volatile-free basis, lot 0063-59-26) of Na-ZS-9 was washed with approximately 31 Liters of DI water at 2 Liter increments over 3 days until the pH of the rinsate reached 7. The material was filtered, dried and washed with DI water. The pH of the resulting material was 7. The H-ZS-9 powder resulting from batch-wise ion exchange and water wash has <12% Na.

As illustrated in this example, water washing is capable of reducing the sodium content of a NA-ZS-9 composition to within a desired range.

EXAMPLE 8

Separate batches of ZS-9 crystals were analyzed using light scatter diffraction techniques. The particle size distribution and other measured parameters are shown in FIGS. 2-4. The d(0.1), d(0.5), and d(0.9) values represent the 10%, 50%, and 90% size values. The cumulative particle size distribution is shown in FIG. 4-6. As can be seen from the following figures, the cumulative volume of particles having a diameter below 3 microns ranges from approximately 0.3% to approximately 6%. In addition, different batches of ZS-9 have different particle size distributions with varying levels of particles having a diameter of less than 3 microns.

EXAMPLE 9

Crystals of ZS-9 were subject to screening to remove small diameter particles. The resulting particle size distribution of the ZS-9 crystals screened using different size screens was analyzed. As illustrated in the following figures, the fraction of particles having a diameter below 3 microns can be lowered and eliminated using an appropriate mesh size screen. Without screening, approximately 2.5% percent of the particles had a diameter of below 3 microns. See FIG. 5. Upon screening with a 635 mesh screen, the fraction of particles having a diameter below 3 microns was reduced to approximately 2.4%. See FIG. 6. Upon screening with a 450 mesh screen, the fraction of particles having a diameter below 3 microns was reduced further to approximately 2%. See FIG. 7. When a 325 mesh screen is used, the fraction of particles having a diameter below 3 microns is further reduced to approximately 0.14%. See FIG. 8. Finally, a 230 mesh screen reduces the fraction of particles below 3 microns to 0%. See FIG. 9.

The screening techniques presented in this example illustrate that particle size distributions may be obtained for ZS-9 that provide little or no particles below 3 microns. It will be appreciated that ZS-9 according to Example 5 or H-ZS-9 according to Examples 6 and 7 may be screened as taught in this example to provide a desired particle size distribution. Specifically, the preferred particle size distributions disclosed herein may be obtained using the techniques in this example for both ZS-9 and H-ZS-9.

EXAMPLE 10

A 14-Day repeat dose oral toxicity study in Beagle Dogs with Recovery was conducted. This GLP compliant oral toxicity study was performed in beagle dogs to evaluate the potential oral toxicity of ZS-9 when administered at 6 h intervals over a 12 h period, three times a day, in food, for at least 14 consecutive days. In the Main Study ZS-9 was administered to 3/dogs/sex/dose at dosages of 0 (control), 325, 650 or 1300 mg/kg/dose. An additional 2 dogs/sex/dose, assigned to the Recovery Study, received 0 or 1300 mg/kg/dose concurrently with the Main study animals and were retained off treatment for an additional 10 days. A correction factor of 1.1274 was used to correct ZS-9 for water content. Dose records were used to confirm the accuracy of dose administration.

During the acclimation period (Day −7 to Day −1) dogs were trained to eat 3 portions of wet dog chow at 6 h intervals. During treatment the requisite amount of test article (based on the most recently recorded body weight) was mixed with ~100 g of wet dog food and offered to the dogs at 6 h intervals. Additional dry food was offered following consumption of the last daily dose. Each dog received the same amount of wet dog feed. Body weights were recorded at arrival and on Days −2, −1, 6, 13 and 20. Clinical observations were performed twice daily during the acclimation, treatment and recovery periods. Wet and dry food consumption was measured daily during the treatment period. Blood and urine samples for analysis of serum chemistry, hematology, coagulation and urinalysis parameters were collected pretest (Day −1) and Day 13. Ophthalmologic examinations were performed pretest (Day −6/7) and on Day 7 (females) or 8 (males). Electrocardiographic assessments were performed pretest (Day −1) and on Day 11. At study termination (Day 14—Main Study and Day 24—Recovery Study), necropsy examinations were performed, protocol specified organ weights were weighed, and selected tissues were microscopically examined.

Oral administration of 325, 650 and 1300 mg ZS-9/kg/dose with food, three times a day at 6 h intervals over a 12-hour period for 14 days was well tolerated. Clinical signs were limited to the observation of white material, presumed to be test article, in the feces of some dogs at the 325 mg/kg/dose and in all animals receiving 650 mg/kg/dose during the second week of treatment. There were no adverse effects on body weight, body weight change, food consumption, hematology and coagulation parameters or ophthalmoscopic and ECG evaluations.

There were no macroscopic findings associated with administration of ZS-9. Microscopically, minimal to mild focal and/or multifocal inflammation was observed in the kidneys of treated animals but not in Control animals. The lesions had similar incidence and severity at 650 and 1300 mg/kg and were less frequent and severe at 325 mg/kg. In some dogs the inflammation was unilateral rather than bilateral and in some cases was associated with inflammation in the urinary bladder and origin of the ureter. Taken together these observations suggest that factors other than direct renal injury, such as alterations in urine composition of ZS-9-treated dogs may have resulted in increased susceptibility to subclinical urinary tract infections, even though no microorganisms were observed in these tissues. In recovery animals the inflammation was completely resolved in females and partly resolved in males suggesting that whatever the cause of the inflammation it was reversible following cessation of dosing. The increased incidence of mixed leukocyte inflammation observed in Beagle dogs treated with ZS-9 is summarized below.

Summary of Inflammation in Kidneys
Terminal Necropsy (TN): Day 14

| | | Dose | | | | | | | |
|---|---|---|---|---|---|---|---|---|---|
| | | 0 mg/kg | | 325 mg/kg | | 650 mg/kg | | 1,300 mg/kg | |
| Sex | | M | F | M | F | M | F | M | F |
| Number of Animals | | 3 | 3 | 3 | 3 | 3 | 3 | 3 | 3 |
| Left | Incidence | 0/3 | 0/3 | 0/3 | 2/3 | 2/3 | 3/3 | 3/3 | 3/3 |
| Kidney | minimal | 0/3 | 0/3 | 0/3 | 2/3 | 2/3 | 2/3 | 3/3 | 1/3 |
| | mild | 0/3 | 0/3 | 0/3 | 0/3 | 0/3 | 1/3 | 0/3 | 2/3 |
| Right | Incidence | 0/3 | 0/3 | 1/3 | 1/3 | 2/3 | 3/3 | 2/3 | 2/3 |
| Kidney | minimal | 0/3 | 0/3 | 1/3 | 1/3 | 2/3 | 1/3 | 2/3 | 0/3 |
| | mild | 0/3 | 0/3 | 0/3 | 0/3 | 0/3 | 2/3 | 0/3 | 2/3 |
| Both | Incidence | 0/6 | 0/6 | 1/6 | 3/6 | 4/6 | 6/6 | 5/6 | 5/6 |
| Kidneys | minimal | 0/6 | 0/6 | 1/6 | 3/6 | 4/6 | 3/6 | 5/6 | 1/6 |
| | mild | 0/6 | 0/6 | 0/6 | 0/6 | 0/6 | 3/6 | 0/6 | 4/6 |
| Sum of Severity Scores | | 0 | 0 | 2 | 3 | 4 | 9 | 5 | 9 |
| | | 0 | | 5 | | 13 | | 14 | |
| Mean Group Severity Scores | | 0.00 | | 0.83 | | 2.17 | | 2.33 | |

Minimal acute urinary bladder inflammation and unidentified crystals were also observed in the renal pelvis and urine of females dosed at 650 mg/kg/dose as summarized below Summary of Crystals observed at the 650 mg/kg/dose

| | Animal No | | |
|---|---|---|---|
| | 4420 | 4421 | 4422 |
| Unidentified crystals in urine | + | − | + |
| Crystals in renal pelvis | − | + | − |
| Urinary bladder acute inflammation | + | + | − |

Crystals were not identified in group 2 or 4 females or in any ZS-9 treated males.

In both studies it was noted that urinary pH was elevated compared to control and it was postulated that the change in urinary pH and/or urinary composition affected urine solute solubility resulting in crystal formation that caused urinary tract irritation and/or increased susceptibility to urinary tract infections (UTIs).

The description of the urinary crystals (long thin spiky clusters) coupled with the particle size profile and insolubility of test article make it very unlikely that these crystals are ZS-9.

EXAMPLE 11

Crystals of ZS-9 are prepared and designated "ZS-9 Unscreened." Screening in accordance with the procedures of Example 10 is conducted on a sample of ZS-9 crystals and the screened sample is designated "ZS-9>5 µm." Another sample of Crystals of ZS-9 undergo an ion exchange in accordance with the procedures of Example 6 above and are then screened in accordance with the procedures of Example 10. The resulting H-ZS-9 crystals are designated "ZS-9+>5 µm."

The following 14-day study is designed to show the effect of particle size and particle form on the urinary pH and presence of crystals in the urine. The compounds above are administered to beagles orally by mixing with wet dog food. The regimen is administered 3 times a day at 6 hour intervals over a 12 hour period in the following manner:

Study Design

| Group | mg/kg/dose* | Female |
|---|---|---|
| Control | 0 | 3 |
| ZS-9 Unscreened | 750 | 3 |
| ZS-9 >5 µm | 750 | 3 |
| ZS-9 + >5 µm | 750 | 3 |
| ZS-9 Unscreened | 100 | 3 |
| ZS-9 >5 µm | 100 | 3 |
| ZS-9 + >5 µm | 100 | 3 |
| NaHCO$_3$ | 50 | 3 |

* uncorrected for water
ZS-9+ = pH neutral crystal

| Total number of dogs | 24 females |
|---|---|
| Age | 5 months of age on arrival |
| Acclimation | ≥10 days |
| Test Article Formulation | Mixed with wet dog food |
| Test article administration | Within 30 minutes of administration |
| Dose Formulation Analysis | Dose records will be used to confirm dosing. Weight of any remaining wet food will be recorded. |

The following table outlines the observations, toxicokinetic evaluation, laboratory investigation (hematology, urinalysis), and terminal procedures.

| Observations | |
|---|---|
| Mortality & Signs of ill health or reaction to treatment | Twice daily (after treatment and evening) including feces assessment |
| Detailed Exam | During acclimation, weekly on study |
| Body Weights | Arrival, Day −1, Day 7 and 14 |
| Food Consumption | Daily (Wet and Dry food) |
| Ophthalmoloscopy | None |
| Toxicokinetic (for potential Zr analysis) | |
| 3 × 1 ml whole blood/sample with sample weights recorded | Day −1: Pre-dose Day 13: Pre-dose and 4 h post 2$^{nd}$ dose |
| Laboratory Investigations | |
| Hematology/Clinical chemistry (see list) | Pretreatment and during Weeks 1 and 2 on study |
| Urinalysis (see list) | Pretreatment and during Weeks 1 and 2 on study (Metabolic cage, urine sample to be kept cool) Remaining urine aliquoted and retained frozen for possible future Zr analysis |
| Terminal Procedures | |
| Necropsy | All animals regardless of mode of death. All tissues collected into NBF (see list) |
| Histopathology | Urinary tract only (Kidney and bladder) |

These tests show that the ZSs of the present invention are particularly suitable for the treatment of hyperkalemia.

EXAMPLE 12

ZS-9 crystals were prepared by reaction in a standard 5-G crystallization vessel.

The reactants were prepared as follows. A 22-L Morton flask was equipped with an overhead stirrer, thermocouple, and an equilibrated addition funnel. The flask was charged with deionized water (3.25 L). Stirring was initiated at approximately 100 rpm and sodium hydroxide (1091 g NaOH) was added to the flask. The flask contents exothermed as the sodium hydroxide dissolved. The solution was stirred and cooled to less than 34° C. Sodium silicate solution (5672.7 g) was added. To this solution was added zirconium acetate solution (3309.5 g) over 43 minutes. The resulting suspension was stirred for another 22 minutes. Seed crystals of ZS-9 (223.8 g) were added to the reaction vessel and stirred for approximately 17 minutes.

The mixture was transferred to a 5-G Parr pressure vessel with the aid of deionized water (0.5 L). The vessel had smooth walls and a standard agitator. The reactor did not have a cooling coil present. The vessel was sealed and the reaction mixture was stirred at approximately 275-325 rpm and heated to 185+/−10° C. over 4 hours, then held at 184-186° C. and soaked for 72 hours. Finally, the reactants were then cooled to 80° C. over 12.6 hours. The resulting white solid was filtered with the aid of deionized water (18 L). The solids were washed with deionized water (125 L) until the pH of the eluting filtrate was less than 11 (9.73). The wet cake was dried in vacuo (25 inches Hg) for 48 hours at 95-105° C. to give 2577.9 g (107.1%) of ZS-9 as a white solid.

The XRD plot of the ZS-9 obtained in this example is shown in FIG. 10. The FTIR plot of this material is shown in FIG. 11. These XRD and FTIR spectra are characterized by the presence of absorption peaks typically associated with the ZS-11 crystalline form. In addition, the peaks that are associated with ZS-9 exhibit significant spreading due to crystal impurities (e.g. the presence of ZS-11 crystals in a ZS-9 composition). For example, the FTIR spectra shows significant absorption around 764 and 955 cm$^{-1}$. The XRD plot for this example exhibits significant noise and poorly defined peaks at 2-theta values of 7.5, 32, and 42.5.

EXAMPLE 13

High capacity ZS-9 crystals were prepared in accordance with the following representative example.

The reactants were prepared as follows. A 22-L Morton flask was equipped with an overhead stirrer, thermocouple, and an equilibrated addition funnel. The flask was charged with deionized water (8,600 g, 477.37 moles). Stirring was initiated at approximately 145-150 rpm and sodium hydroxide (661.0 g, 16.53 moles NaOH, 8.26 moles Na2O) was added to the flask. The flask contents exothermed from 24° C. to 40° C. over a period of 3 minutes as the sodium hydroxide dissolved. The solution was stirred for an hour to allow the initial exotherm to subside. Sodium silicate solution (5,017 g, 22.53 mole SO2, 8.67 moles Na2O) was added. To this solution, by means of the addition funnel, was added zirconium acetate solution (2,080 g, 3.76 moles ZrO2) over 30 min. The resulting suspension was stirred for and additional 30 min.

The mixture was transferred to a 5-G Parr pressure vessel Model 4555 with the aid of deionized water (500 g, 27.75 moles). The reactor was fitted with a cooling coil having a serpentine configuration to provide a baffle-like structure within the reactor adjacent the agitator. The cooling coil was not charged with heat exchange fluid as it was being used in this reaction merely to provide a baffle-like structure adjacent the agitator.

The vessel was sealed and the reaction mixture was stirred at approximately 230-235 rpm and heated from 21° C. to 140-145° C. over 7.5 hours and held at 140-145° C. for 10.5 hours, then heated to 210-215° C. over 6.5 hours where the maximum pressure of 295-300 psi was obtained, then held at 210-215° C. for 4 1.5 hours. Subsequently, the reactor was cooled to 45° C. over a period of 4.5 hours. The resulting white solid was filtered with the aid of deionized water (1.0 KG). The solids were washed with deionized water (40 L) until the pH of the eluting filtrate was less than 11 (10.54). A representative portion of the wet cake was dried in vacuo (25 inches Hg) overnight at 100° C. to give 1,376 g (87.1%) of ZS-9 as a white solid.

The XRD plot of the ZS-9 obtained is shown in FIG. 12. The FTIR plot of this material is shown in FIG. 13. These XRD and FTIR spectra, when compared to those for Example 12 (FIGS. 10-11), exhibited well-delineated peaks without spreading and the absence of peaks associated with crystalline forms other than ZS-9 (e.g., ZS-11 peaks). This example illustrates how the presence of a baffle-like structure within the reactor drastically and unexpectedly improves the quality of the thus obtained crystals. Although not wishing to be bound by theory, the inventors understand that baffles provide added turbulence which lifts the solids (i.e., crystals) and results in a more even suspension of crystals within the reaction vessel while the reaction is ongoing. This improved suspension allows for more complete reaction to the desired crystalline form and reduces the presence of unwanted crystalline forms of ZS in the end product.

EXAMPLE 14

The potassium exchange capacity (KEC) of ZS (ZS-9) was determined according to the following protocol.

This test method used a HPLC capable of gradient solvent introduction and cation exchange detection. The column was an IonPac CS12A, Analytical (2×250 mm). The flow rate was 0.5 mL/minute with a run time of approximately 8 minutes. The column temperature was set to 35° C. The injection volume was 10 μL and the needle wash was 250 μL. The pump was operated in Isocratic mode and the solvent was DI water.

A stock standard was prepared by accurately weighing and recording the weight of about 383 mg of potassium chloride (ACS grade), which was transferred into a 100-1 μL plastic volumetric flask. The material was dissolved and diluted to volume with diluent followed by mixing. The stock standard had a K$^+$ concentration of 2000 ppm (2 mg/mL). Samples were prepared by accurately weighing, recording, and transferring about 112 mg of ZS-9 into a 20 mL plastic vial. 20.0 mL of the 2000 ppm potassium stock standard solution was pipetted into the vial and the container was closed. The sample vials were placed onto a wrist action shaker and were shook for at least 2 hours but not more than 4 hours. The sample preparation solution was filtered through a 0.45 pm PTFE filter into a plastic container. 750 pL of the sample solution was transferred into a 100-mL plastic volumetric flask. The sample was diluted to volume with DI water and mixed. The initial K$^+$ concentration was 15 ppm (15 μg/mL).

The samples were injected into the HPLC. FIG. 14 shows an example of the blank solution chromatogram. FIG. 15 shows an example of the assay standard solution chromatogram. FIG. 16 shows an exemplary sample chromatogram. The potassium exchange capacity was calculated using the following formula:

$$KEC = \frac{\frac{(IC - FC) \times V}{Eq\ wt.}}{Wt_{SPL} \times \frac{(100\% - \%\ Water)}{100\%} \times \frac{1\ g}{1000\ mg}}$$

KEC is the potassium exchange capacity in mEq/g. The initial concentration of potassium (ppm) is IC. The final concentration of potassium (ppm) is FC. The equivalent weight (atomic weight/valence) is Eq wt. The volume (L) of standard in sample preparation is V. The weight of ZS-9 (mg) used for sample preparation is $Wt_{spl}$. The percent (%) of water content (LOD) is % water.

Three samples of ZS-9 produced in accordance with the procedures of Example 12, i.e., in a reactor without baffles (e.g., internal cooling coil structure), were tested for potassium exchange capacity (KEC) in accordance with the above-referenced procedure. Likewise, three samples of ZS-9 produced in accordance with Example 13 in a reactor having cooling coils serving as baffles were tested in accordance with this procedure. The results in Table 3 below show that the procedure of Example 13 and the presence of baffles within the crystallization vessel resulted in a dramatic increase in the potassium exchange capacity.

TABLE 3

Potassium Exchange Capacity (KEC)

| Example 12 (Without baffles) | | Example 13 (With baffles) | |
|---|---|---|---|
| Lot 5368-10311A | 2.3 meq/gm | Lot 2724-9A | 3.9 meq/gm |
| Lot 5368-12211A | 1.7 meq/gm | Lot 2724-13D | 3.8 meq/gm |
| Lot 5368-13811A | 1.8 meq/gm | Lot 2724-18F | 3.8 meq/gm |

EXAMPLE 15

The use of an internal cooling coil to provide a baffle-like structure within the reactor is only feasible for small reactors on the order of 5-gallons because larger reactors cannot be easily fitted with, and typically do not utilized, cooling coils.

The inventors have designed a reactor for larger-scale production of high purity, high-KEC ZS-9 crystals. Large-scale reactors typically utilize a jacket for achieving heat transfer to the reaction chamber rather than coils suspended within the reaction chamber. A conventional 200-L reactor 100 is shown in FIG. 17. The reactor 100 has smooth walls and an agitator 101 extending into the center of the reaction chamber. The reactor 100 also has a thermowell 102 and a bottom outlet valve 103. The inventors have designed an improved reactor 200, FIG. 18, which also has an agitator 201, thermowell 202, and bottom outlet valve 203. The improved reactor 200 has baffle structures 204 on its sidewalls, which in combination with the agitator 201 provide significant lift and suspension of the crystals during reaction and the creation of high purity, high KEC ZS-9 crystals. The improved reactor can also include a cooling or heating jacket for controlling the reaction temperature during crystallization in addition to the baffle structures 204. The details of an exemplary and non-limiting baffle design is shown in FIG. 19. Preferably the reactor has a volume of at least 20-L, more preferably 200-L or more, or within the range of 200-L to 30,000-L.

EXAMPLE 16

The microporous ZS compositions disclosed herein have been found to absorb a significant amount of calcium from the patients body during treatment for hyperkalemia. In this example, the compositions of Examples 1-9 and 12-13 are administered to hypercalcemic patients who are being treated for hyperkalemia. The administration of these compositions to hypercalcemic patients suffering from hyperkalemia reduces both potassium and calcium levels in the patient.

EXAMPLE 17

The compositions of Examples 1-9 and 12-13 are further processed to load the compositions with calcium, magnesium or mixtures of both calcium and magnesium. The crystals of ZS of Examples 1-9 and 12-13 are obtained. The crystals are then subject to an ion exchange process by contacting the crystals with a solution containing calcium ions, magnesium ions, or both calcium and magnesium at a concentration of between 10 and 100 ppm. The resultant ZS compositions are effective at absorbing potassium while avoiding the absorption of excess calcium.

EXAMPLE 18

ZS crystals are contacted with calcium solutions having calcium concentrations of 30 ppm, 45 ppm, and 60 ppm. The amount of calcium uptake is determined for each concentration after the saturation step in addition to determining a baseline level for each concentration prior to saturation. Once the ZS crystal has been saturated, the supernatant is pulled off and replaced with an equal volume of USP grade water and agitated for 20 minutes. This step is conducted twice. After completion of the second wash step, the water is removed and the sample is centrifuged at 3000 rpm for 5 minutes. Then the ZS crystal samples are placed in an oven at 75° C. until dry, approximately 2 hours. Once the samples are dry, they are prepared as in Example 14 to determine the potassium exchange capacity. The amount of unbound calcium is determined as well.

EXAMPLE 19

ZS crystals are contacted with magnesium solutions having magnesium at concentrations of 30 ppm, 45 ppm, and 60 ppm. The amount of calcium uptake is determined for each concentration after the saturation step in addition to determining a baseline level for each concentration prior to saturation. Once the ZS crystal has been saturated, the supernatant is pulled off and replaced with an equal volume of USP grade water and agitated for 20 minutes. This step is conducted twice. After completion of the second wash step, the water is removed and the sample is centrifuged at 3000 rpm for 5 minutes. Then the ZS crystal samples are placed in an oven at 75° C. until dry, approximately 2 hours. Once the samples are dry, they are prepared as in Example 14 to determine the potassium exchange capacity. The amount of unbound magnesium is determined as well.

EXAMPLE 20

ZS crystals are contacted with a solution comprising both calcium and magnesium (at a ratio range of 1:10 to 10:1), where the solution has a final calcium and magnesium concentration of 30 ppm, 45 ppm, and 60 ppm. The amount of calcium uptake is determined for each concentration after the saturation step in addition to determining a baseline level for each concentration prior to saturation. Once the ZS crystal has been saturated, the supernatant is pulled off and replaced with an equal volume of USP grade water and agitated for 20 minutes. This step is conducted twice. After completion of the second wash step, the water is removed and the sample is centrifuged at 3000 rpm for 5 minutes. Then the ZS crystal samples are placed in an oven at 75° C. until dry, approximately 2 hours. Once the samples are dry, they are prepared as in Example 14 to determine the potassium exchange capacity. The amount of unbound calcium and magnesium is determined as well.

EXAMPLE 21

The crystals of ZS of Examples 1-9 and 12-13 are administered to hypercalcemic patients to treat hyperkalemia. These compositions reduce levels of calcium and potassium in the patients.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

The invention claimed is:

1. A particulate cation exchange composition comprising a zirconium silicate of formula (I):

(I)

where
A is a potassium ion, sodium ion, rubidium ion, cesium ion, calcium ion, magnesium ion, hydronium ion or mixtures thereof,
M is at least one framework metal, wherein the framework metal is hafnium (4+), tin (4+), niobium (5+), titanium (4+), cerium (4+), germanium (4+), praseodymium (4+), terbium (4+) or mixtures thereof,
"p" has a value from about 1 to about 20,
"x" has a value from 0 to less than 1,
"n" has a value from about 0 to about 12,
"y" has a value from 0 to about 12,
"m" has a value from about 3 to about 36 and $1 \leq n+y \leq 12$,
wherein the particles of zirconium silicate exhibit a uniform microporous structure and a median particle size of greater than 3 microns and less than 7% of the particles in the composition have a diameter less than 3 microns, and the zirconium silicate exhibits a sodium content below 12% by weight and a divalent cation content from 1 to 100 ppm,
wherein the divalent cation is a combination of calcium and magnesium in a ratio range of 1:10 to 10:1.

2. The composition of claim 1, wherein the sodium content is less than 6% by weight.

3. The composition of claim 1, wherein the sodium content is between 0.05 to 3% by weight.

4. The composition of claim 1, wherein the sodium content is less than 0.01% by weight.

5. The composition of claim 1, wherein less than 4% of the particles in the composition have a diameter less than 3 microns.

6. The composition of claim 1, wherein less than 1% of the particles in the composition have a diameter less than 3 microns.

7. The composition of claim 1, wherein the median particle size ranges from 5 to 1000 microns.

8. The composition of claim 1, wherein the median particle size ranges from 20 to 100 microns.

9. The composition of claim 1, wherein the composition exhibits an x-ray powder diffraction pattern generated using a copper K-alpha radiation source of:

| d(A) |
| --- |
| 5.9-6.7 |
| 5.3-6.1 |
| 2.7-3.5 |
| 2.0-2.8 |
| 1.6-2.4. |

10. The composition of claim 1, wherein the composition exhibits a calcium content in the range of 5 to 30 ppm.

11. A pharmaceutical product comprising the composition of claim 1 in capsule or tablet form.

12. A cation exchange composition comprising a zirconium silicate of formula (I):

(I)

where
A is a potassium ion, sodium ion, rubidium ion, cesium ion, calcium ion, magnesium ion, hydronium ion or mixtures thereof,
M is at least one framework metal, wherein the framework metal is hafnium (4+), tin (4+), niobium (5+), titanium (4+), cerium (4+), germanium (4+), praseodymium (4+), terbium (4+) or mixtures thereof,
"p" has a value from about 1 to about 20,
"x" has a value from 0 to less than 1,
"n" has a value from about 0 to about 12,
"y" has a value from 0 to about 12,
"m" has a value from about 3 to about 36 and $1 \leq n+y \leq 12$,
wherein the zirconium silicate exhibits a uniform microporous structure and a median particle size of greater than 3 microns and less than 7% of the particles in the composition have a diameter less than 3 microns, and the zirconium silicate exhibits a sodium content below 12% by weight and a divalent cation content between 1 and 100 ppm, the divalent cation being calcium, magnesium, or a combination of calcium and magnesium.

13. The composition of claim 12, wherein the potassium exchange capacity is between 3.7 and 4.7 meq/g.

14. The composition of claim 12, wherein the composition exhibits an x-ray powder diffraction pattern generated using a copper K-alpha radiation source of:

| d(A) |
| --- |
| 5.9-6.7 |
| 5.3-6.1 |
| 2.7-3.5 |
| 2.0-2.8 |
| 1.6-2.4. |

15. The composition of claim 12, wherein the potassium exchange capacity is greater than 4.0 meq/g.

16. The composition of claim 12, wherein the potassium exchange capacity is greater than 4.4 meq/g.

17. The composition of claim 12, wherein the FTIR spectra of the composition does not include absorption peaks at approximately 764 and 955 cm$^{-1}$.

18. The composition of claim 12, wherein the XRD plot of the composition does not indicate significant peaks at 2-theta values of 7.5, 32, or 42.5.

19. The composition of claim 12, wherein the composition exhibits a calcium content in the range of 5 to 30 ppm.

20. A pharmaceutical product comprising the composition of claim 12 in capsule or tablet form.

21. A method for treatment of hyperkalemia comprising administering the composition of claim 1 to a patient in need thereof.

22. The method of claim 21, wherein the patient is suffering from acute hyperkalemia.

23. The method of claim 22, wherein the patient is administered a dose of approximately 0.7 to 1,500 mg/Kg/day.

24. The method of claim 22, wherein the patient is administered a dose of approximately 500 to 1,000 mg/Kg/day.

25. The method of claim 22, wherein the patient is administered a dose of approximately 700 mg/Kg/day.

26. The method of claim 21, wherein the patient is suffering from chronic hyperkalemia.

27. The method of claim 26, wherein the patient is administered a dose of approximately 0.25 to 100 mg/Kg/day.

28. The method of claim 26, wherein the patient is administered a dose of approximately 10 to 70 mg/Kg/day.

29. The method of claim 26, wherein the patient is administered a dose of approximately 50 mg/Kg/day.

30. The method of claim 21, wherein the patient is at risk for congestive heart failure.

31. The method of claim 21, wherein the patient has edema from elevated sodium levels.

32. A method for treatment of hyperkalemia comprising administering the composition of claim 12 to a patient in need thereof.

33. A method for making the composition of claim 1 comprising:
   providing a reaction mixture comprising sodium silicate and zirconium acetate in a reactor;
   agitating the reaction mixture with an agitator in the presence of one or more baffle-like structure;
   obtaining the cation exchange composition from the reactor, wherein the presence of the baffle-like structures increases the crystalline purity and potassium exchange capacity of the resulting composition compared to the like composition made in a reactor without baffle-like structures; and
   contacting the composition with divalent cations in a concentration ranging from 6 1 to 100 ppm, wherein the divalent cation is a combination of calcium and magnesium in a ratio range of 1:10 to 10:1.

34. The method of claim 33, further comprising a step of contacting the zirconium silicate with a dilute solution of strong acid and/or water.

35. The method of claim 33, further comprising a step of screening the cation exchange composition to produce a desired particle size distribution.

36. The method of claim 25, wherein the microporous zirconium silicate has a potassium exchange capacity greater than 2.5 meq/g.

* * * * *